(12) United States Patent
Khan

(10) Patent No.: US 9,745,342 B2
(45) Date of Patent: Aug. 29, 2017

(54) NMDA RECEPTOR MODULATORS AND PRODRUGS, SALTS, AND USES THEREOF

(71) Applicant: Naurex, Inc., Parisppany, NJ (US)

(72) Inventor: Amin Khan, Evanston, IL (US)

(73) Assignee: Naurex, Inc., Evanston, IL (US)

( * ) Notice: Subject to any disclaimer, the term of this patent is extended or adjusted under 35 U.S.C. 154(b) by 0 days.

(21) Appl. No.: 15/033,031

(22) PCT Filed: Oct. 27, 2014

(86) PCT No.: PCT/US2014/062367
§ 371 (c)(1),
(2) Date: Apr. 28, 2016

(87) PCT Pub. No.: WO2015/065891
PCT Pub. Date: May 7, 2015

(65) Prior Publication Data
US 2016/0244485 A1    Aug. 25, 2016

Related U.S. Application Data

(60) Provisional application No. 61/896,308, filed on Oct. 28, 2013.

(51) Int. Cl.
| | | |
|---|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 5/12* | (2006.01) |
| *C07K 7/56* | (2006.01) |
| *C07K 5/117* | (2006.01) |
| *A61K 38/00* | (2006.01) |

(52) U.S. Cl.
CPC ............ *C07K 5/126* (2013.01); *C07K 5/1024* (2013.01); *C07K 7/56* (2013.01); *A61K 38/00* (2013.01)

(58) Field of Classification Search
CPC ................................ A61K 38/00; C07K 16/00
See application file for complete search history.

(56) References Cited

U.S. PATENT DOCUMENTS

2009/0263858 A1    10/2009   Nishimura et al.

FOREIGN PATENT DOCUMENTS

WO    2012-149389    11/2012

OTHER PUBLICATIONS

Burgdorf, Jeffrey et al, The Effects of Selective Breeding for Differential Rates of 50-kHz Ultrasonic Vocalizations on Emotional Behavior in Rats, Dev Psychobiol, 2009, 34-46, 51.
Foster, Alan et al, Taking Apart NMDA Receptors, Nature, Oct. 1987, 395-396, 329.
Kaz, Bradley et al, Structure-Based Design of High Affinity Streptavidin Binding Cyclic Peptide Ligands Containing Thioether Cross-Links, J Am Chem Soc, 1995, 8541-8547, 117.
Mayer, Mark et al, Excitatory Amino Acid Receptors, Second Messengers and Regulation of Intracellular Ca2+ in Mammalian Neurons, Trends in Pharmacological Sciences, 1990, 254-260(Abstract Only), 6.
PubChem, Compound Summary for CID 14160063, Create Date: Dec. 5, 2007. [retrieved on Dec. 5, 2014]. Retrieved from the internet.    Url:https://pubchem.ncbi.nlm.nih.gov/compound/14160063.
PubChem, Compound Summary for CID 18238417, Create Date: Dec. 5, 2007. [retrieved on Dec. 5, 2014]. Retrieved from the internet.    Url:https://pubchem.ncbi.nlm.nih.gov/compound/18238417.
Urwyler, Stephan et al, Drug Design, in Vitro Pharmacology, and Structure-Activity Relationships of 3-Acylamino-2-aminopropionic Acid Derivatives, a Novel Class of Partial Agonists at the Glycine Site on the N-Methyl-D-aspartate (NMDA) Receptor Complex, J Med Chem, 2009, 5093-5107, 52.
Zhang, Xiao-Lei et al, A NMDA Receptor Glycine Site Partial Agonist, GLYX-13, Simultaneously Enhances LTP and Reduces LTD at Schaffer Collateral-CA1 Synapses in Hippocampus, Neuropharmacology, 2008, 1238-1250, 55.

*Primary Examiner* — Hasan Ahmed
*Assistant Examiner* — Kaipeen Yang
(74) *Attorney, Agent, or Firm* — Andrew Chien

(57) ABSTRACT

Disclosed are compounds having enhanced potency in the modulation of NMD A receptor activity. Such compounds are contemplated for use in the treatment of diseases and disorders, such as learning, cognitive activities, and analgesia, particularly in alleviating and/or reducing neuropathic pain. Orally available formulations and other pharmaceutically acceptable delivery forms of the compounds, including intravenous formulations, are also disclosed.

13 Claims, 4 Drawing Sheets

NMDA RECEPTOR MODULATORS AND PRODRUGS, SALTS, AND USES THEREOF

CROSS REFERENCE TO RELATED APPLICATIONS

This application claims the benefit of U.S. Provisional Application No. 61/896,308, filed Oct. 28, 2013, which is incorporated herein by reference in its entirety.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for an orally deliverable forms of such compounds.

SUMMARY

Provided herein, at least in part, are compounds that are NMDA modulators, for example, partial agonists of NMDA. For example, disclosed herein are compounds represented by the formula:

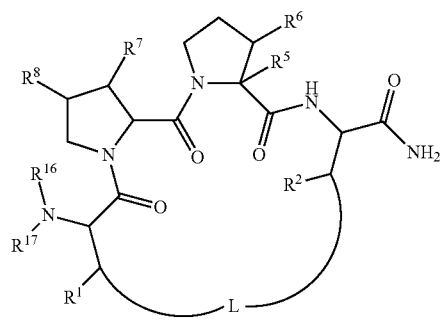

and pharmaceutically acceptable salts, stereoisomers, metabolites, and hydrates thereof, wherein: L, $R^1$, $R^2$, $R^5$, $R^6$, $R^7$, $R^8$, $R^{16}$, and $R^{17}$ are as defined below.

In another aspect, disclosed herein are compounds represented by the formula:

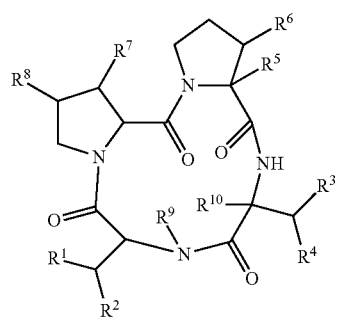

and pharmaceutically acceptable salts, stereoisomers, metabolites, and hydrates thereof, wherein: $R^1$, $R^2$, $R^3$, $R^4$, $R^5$, $R^6$, $R^7$, $R^8$, $R^9$, and $R^{10}$ are as defined below.

In yet another aspect, disclosed herein are compounds represented by the formula:

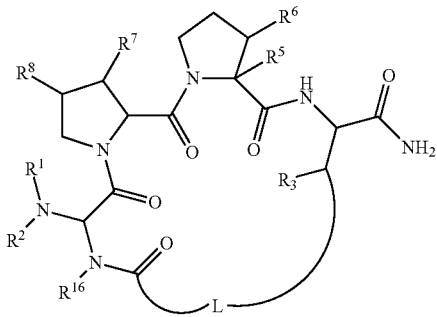

and pharmaceutically acceptable salts, stereoisomers, metabolites, and hydrates thereof, wherein: L, $R^1$, $R^2$, $R^3$, $R^5$, $R^6$, $R^7$, $R^8$, and $R^{16}$ are as defined below.

In still another aspect, disclosed herein are compounds represented by the formula:

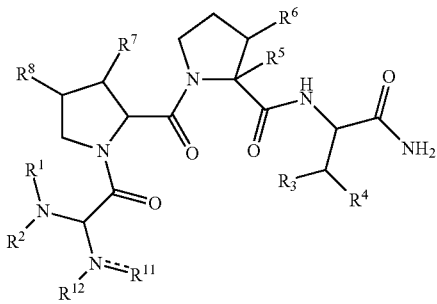

and pharmaceutically acceptable salts, stereoisomers, metabolites, and hydrates thereof, wherein: $R^1$, $R^2$, $R^3$, $R^4$, $R^5$, $R^6$, $R^7$, $R^8$, $R^{11}$, and $R^{12}$ are as defined below.

In yet another aspect, disclosed herein are compounds represented by the formula:

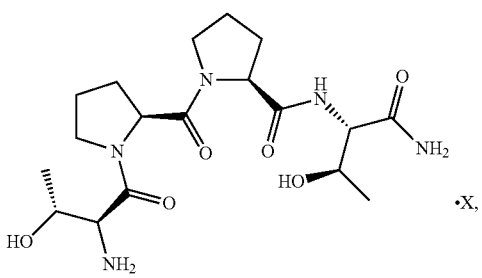

wherein X is selected from the group consisting of:

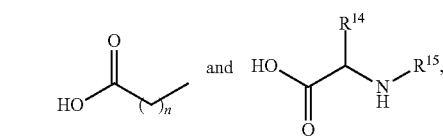

wherein:
n is an integer from 8-20;
$R^{14}$ is selected from the group consisting of hydrogen; $C_1$-$C_6$ alkyl; —($C_1$-$C_6$ alkyl)-phenyl; —($C_1$-$C_6$ alkyl)-phenol; —($C_1$-$C_6$ alkyl)-heteroaryl; —($C_1$-$C_6$ alkyl)-SH; —($C_1$-$C_6$ alkyl)-S—($C_1$-$C_6$ alkyl); —($C_1$-$C_6$ alkyl)-OH; —($C_1$-$C_6$ alkyl)-O—($C_1$-$C_6$ alkyl); —($C_1$-$C_6$ alkyl)-$NH_2$; —($C_1$-$C_6$ alkyl)-NH—($C_1$-$C_6$ alkyl); —($C_1$-$C_6$ alkyl)-guanidine; —($C_1$-$C_6$ alkyl)-C(O)OH; —($C_1$-$C_6$ alkyl)-C(O)O—($C_1$-$C_6$ alkyl); —($C_1$-$C_6$ alkyl)-C(O)$NH_2$;
$R^{15}$ is selected from the group consisting of acyl, alkylsulfonyl, and arylsulfonyl;
$R^{18}$ is hydrogen, or $R^{14}$ and $R^{18}$ together with the atoms to which they are attached form a 4-7 membered ring; and stereoisomers, metabolites, and hydrates thereof.

In still another aspect, disclosed herein are compounds represented by the formula:

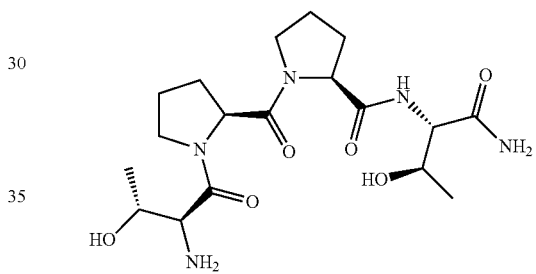

and
a second compound complexed with the first, wherein the second compound is selected from the group consisting of:

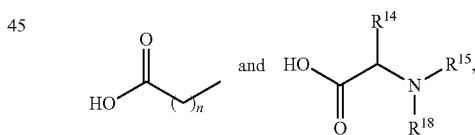

wherein:
n is an integer from 8-20;
$R^{14}$ is selected from the group consisting of hydrogen; $C_1$-$C_6$ alkyl; —($C_1$-$C_6$ alkyl)-phenyl; —($C_1$-$C_6$ alkyl)-phenol; —($C_1$-$C_6$ alkyl)-heteroaryl; —($C_1$-$C_6$ alkyl)-SH; —($C_1$-$C_6$ alkyl)-S—($C_1$-$C_6$ alkyl); —($C_1$-$C_6$ alkyl)-OH; —($C_1$-$C_6$ alkyl)-O—($C_1$-$C_6$ alkyl); —($C_1$-$C_6$ alkyl)-$NH_2$; —($C_1$-$C_6$ alkyl)-NH—($C_1$-$C_6$ alkyl); —($C_1$-$C_6$ alkyl)-guanidine; —($C_1$-$C_6$ alkyl)-C(O)OH; —($C_1$-$C_6$ alkyl)-C(O)O—($C_1$-$C_6$ alkyl); —($C_1$-$C_6$ alkyl)-C(O)$NH_2$;
$R^{15}$ is selected from the group consisting of acyl, alkylsulfonyl, and arylsulfonyl;
$R^{18}$ is hydrogen, or $R^{14}$ and $R^{18}$ together with the atoms to which they are attached form a 4-7 membered ring; and stereoisomers, metabolites, and hydrates thereof.

Also provided herein are pharmaceutically acceptable compositions comprising a disclosed compound, and a pharmaceutically acceptable excipient. For example, such compositions may be suitable for oral administration to a patient.

In another aspect, a method of treating a condition selected from the group consisting of autism, depression, epilepsy, AIDS dementia, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, impulse control disorders, Alzheimer's disease, memory loss that accompanies early stage Alzheimer's disease, attention deficit disorder, ADHD, schizophrenia, anxiety, amelioration of opiate, nicotine addiction, ethanol addition, traumatic brain injury, spinal cord injury, post-traumatic stress syndrome, and Huntington's chorea, in a patient in need thereof is provided. The method comprises administering to the patient a pharmaceutically effective amount of a disclosed compound and pharmaceutically acceptable salts, stereoisomers, metabolites, and hydrates thereof.

DETAILED DESCRIPTION

Figure 1:
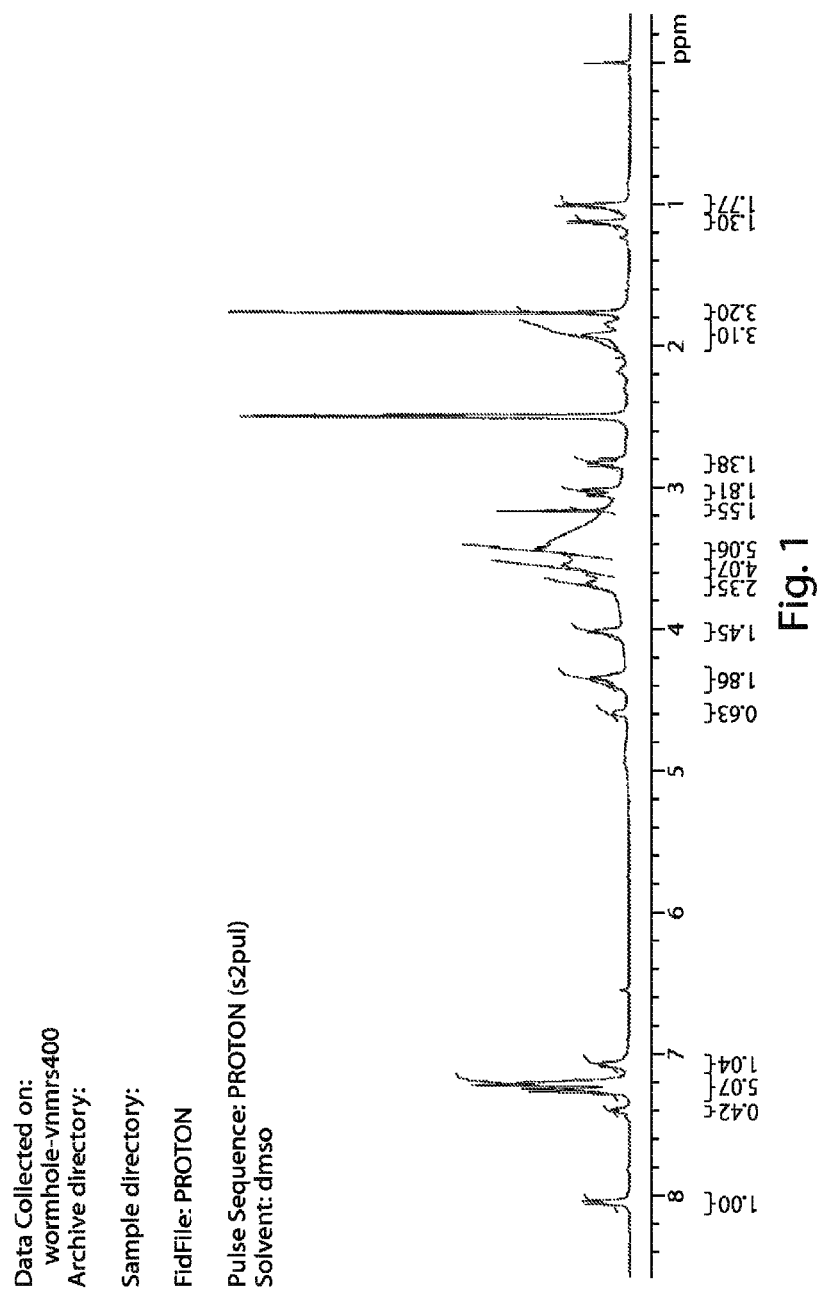
FIG. 1 shows a $^1$H NMR spectrum for NRX-3004.

This disclosure is generally directed to compounds that are capable of modulating NMDA, e.g., NMDA antagonists or partial agonists, and compositions and/or methods of using the disclosed compounds.

Definitions

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroarylthio; oxo; —F; —Cl; —Br; —I; —OH; —NO$_2$; —N$_3$; —CN; —SCN; —SR$^x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$^x$, —C(O)R$^x$; —CO$_2$(R$^x$); —C(O)N(R$^x$)$_2$; —C(NR$^x$)N (R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein each occurrence of R$^x$ independently includes, but is not limited to, hydrogen, halogen, acyl, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "acyl," as used herein, refers to a moiety that includes a carbonyl group. In some embodiments, an acyl group may have a general formula selected from —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —NR$^x$C(O)R$^x$; —NR$^x$C(O)N (R$^x$)$_2$; and —NR$^x$C(O)OR$^x$; wherein each occurrence of R$^x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles (e.g., morpholino, pyrrolidinyl, etc.), which may be optionally substituted with one or more functional groups or may be unsubstituted.

The terms "aryl" and "heteroaryl," as used herein, refer to mono- or polycyclic unsaturated moieties having preferably 3-14 carbon atoms, each of which may be substituted or unsubstituted. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments, "heteroaryl" refers to a mono- or bicyclic heterocyclic ring system having one or two aromatic rings in which one, two, or three ring atoms are heteroatoms independently selected from the group consisting of S, O, and N and the remaining ring atoms are carbon. Non-limiting examples of heteroaryl groups include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as $C_{3-6}$alkenyloxy. Exemplary "alkenyloxy" groups include, but are not limited to allyloxy, butenyloxy, etc.

The term "alkoxy" as used herein refers to an alkyl group attached to an oxygen (—O-alkyl). Exemplary alkoxy groups include, but are not limited to, groups with an alkyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atom, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_1$-$C_6$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

Alkyl, alkenyl and alkynyl groups can optionally be substituted, if not indicated otherwise, with one or more groups selected from alkoxy, alkyl, cycloalkyl, amino, halogen, and —C(O)alkyl. In certain embodiments, the alkyl, alkenyl, and alkynyl groups are not substituted, i.e., they are unsubstituted.

The term "amide" or "amido" as used herein refers to a radical of the form —$R^a$C(O)N($R^b$)—, —$R^a$C(O)N($R^b$)$R^c$—, or —C(O)N$R^b$$R^c$, wherein $R^a$, $R^b$, and $R^c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R^b$, $R^c$, or $R^a$. The amide also may be cyclic, for example $R^b$ and $R^c$, $R^a$ and $R^b$, or $R^a$ and $R^c$ may be joined to form a 3- to 12-membered ring, such as a 3- to 10-membered ring or a 5- to 6-membered ring. The term "carboxamido" refers to the structure —C(O)N$R^b$$R^c$.

The term "amine" or "amino" as used herein refers to a radical of the form —N$R^d$$R^e$, where $R^d$ and $R^e$ are independently selected from hydrogen, alkyl, alkenyl, alkynyl, aryl, arylalkyl, cycloalkyl, haloalkyl, heteroaryl, and heterocyclyl. The amino also may be cyclic, for example, $R^d$ and $R^e$ are joined together with the N to form a 3- to 12-membered ring, e.g., morpholino or piperidinyl. The term amino also includes the corresponding quaternary ammonium salt of any amino group, e.g., —[N($R^d$)($R^e$)($R^f$)]+. Exemplary amino groups include aminoalkyl groups, wherein at least one of $R^d$, $R^e$, or $R^f$ is an alkyl group. In certain embodiment, $R^d$ and $R^e$ are hydrogen or alkyl.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" or "Hal" as used herein refer to F, Cl, Br, or I. The term "haloalkyl" as used herein refers to an alkyl group substituted with one or more halogen atoms.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. The heterocyclic ring may be substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclic group is not substituted, i.e., the heterocyclic group is unsubstituted.

The term "heteroaryloxy" refers to a heteroaryl-O— group.

The term "heterocycloalkyl" is art-recognized and refers to a saturated heterocyclyl group as defined above. The term "heterocyclylalkoxy" as used herein refers to a heterocyclyl attached to an alkoxy group. The term "heterocyclyloxyalkyl" refers to a heterocyclyl attached to an oxygen (—O—), which is attached to an alkyl group.

The term "heterocyclylalkoxy" as used herein refers to a heterocyclyl-alkyl-O— group.

The term "heterocyclyloxy" refers to a heterocyclyl-O— group.

The term "heterocyclyloxyalkyl" refers to a heterocyclyl-O-alkyl- group.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards.

As used in the present disclosure, the term "partial NMDA receptor agonist" is defined as a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ⎯⎯ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

As used in the present disclosure, "NMDA" is defined as N-methyl-d-aspartate.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in defined as that amount needed to give maximal enhancement of a behavior (for example, learning), physiological response (for example, LTP induction), or inhibition of neuropathic pain.

Compounds

Disclosed compounds include those represented by the formula:

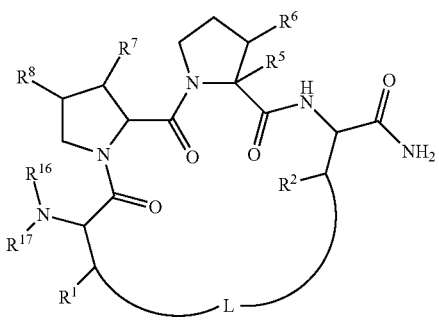

wherein:

$R^1$ and $R^2$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$SOR^x$; —$S(O)_2R^x$; —$NR^x(O)R^x$; —$NR^x(O)N(R^x)_2$; —$NR^xC(O)OR^x$; —$NR^xC(NR^x)N(R^x)_2$; and —$C(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ may be independently selected from the group consisting of hydrogen; halogen; hydroxyl; substituted or unsubstituted $C_1$-$C_6$ alkyl; substituted or unsubstituted $C_1$-$C_6$ alkoxy; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^{16}$ and $R^{17}$ are independently selected from the group consisting of hydrogen; $C_1$-$C_6$ alkyl, optionally substituted by one or more substituents each independently selected from the group consisting of halogen, oxo, and hydroxyl; $C_{2-6}$alkenyl, optionally substituted by one or more substituents each independently selected from the group consisting of halogen, oxo, and hydroxyl; $C_{2-6}$alkynyl, optionally substituted by one or more substituents each independently selected from the group consisting of halogen, oxo, and hydroxyl; $C_{3-6}$cycloalkyl, optionally substituted by one or more substituents each independently selected from the group consisting of $C_{1-6}$alkyl, halogen, oxo, and hydroxyl; phenyl, optionally substituted by one or more substituents each independently selected from the group consisting of $C_{1-6}$alkyl, $C_{1-6}$alkoxy; halogen, and hydroxyl; —C(O)R$^x$; —CO$_2$(R$^x$); —C(O)N(R$^x$)$_2$; —C(NR$^x$)N(R$^x$)$_2$; and —C(R$^x$)$_3$; wherein each occurrence of R$^x$ is independently selected from the group consisting of hydrogen; halogen; $C_{1-6}$alkyl; $C_{2-6}$alkenyl; $C_{2-6}$alkynyl; $C_{3-6}$cycloalkyl; and phenyl; or R$^{16}$ and R$^{17}$, together with N, form a 4-6 membered heterocyclic ring, optionally substituted by one or more substituents each independently selected from the group consisting of $C_{1-6}$alkyl, halogen, oxo, and hydroxyl;

L is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted aryl; and substituted or unsubstituted heteroaryl; and pharmaceutically acceptable salts, stereoisomers, metabolites, and hydrates thereof.

In some embodiments, R$^1$ and R$^2$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$;

R$^b$ may be selected, independently for each occurrence, from the group consisting of halogen; hydroxyl; —NO$_2$; —N$_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkylC$_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

R$^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_x$—, where w is 0, 1, or 2; $C_{1-6}$alkylC$_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^d$ may be selected, independently for each occurrence, from the group consisting of $C_{1-6}$ alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and R$^a$R$^{a'}$N—;

R$^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; $C_{1-4}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; R$^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that NH moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$.

In some embodiments, R$^5$ and R$^6$ may be independently selected from the group consisting of -Q-Ar and hydrogen; wherein Q is independently selected from the group consisting of $C_{1-6}$alkoxy; $C_{1-6}$alkyl; $C_{2-6}$alkenyl; $C_{2-6}$alkynyl; $C_{3-6}$cycloalkyl; heterocyclyl; $C_{3-6}$cycloalkyl-$C_{1-6}$alkyl-; and heterocyclyl-$C_{1-6}$alkyl-; and a bond; and wherein Ar is selected from the group consisting substituted or unsubstituted phenyl or naphthyl, and substituted or unsubstituted heteroaryl; or R$^5$ and R$^6$, together with the atoms to which they are attached, form a substituted or unsubstituted 4-6 membered heterocyclic or cycloalkyl ring; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from $R^e$; wherein $C_{1-6}$alkyl and $C_{1-6}$alkoxy are each independently optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —NO$_2$; —N$_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and R$^a$R$^{a'}$N—;

$R^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

$R^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; and $R^g$ may be selected, independently for each occurrence, from the group consisting of halogen, hydroxyl, —NO$_2$; —N$_3$; —CN; —SCN; $C_{1-6}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2.

In some cases, $R^7$ and $R^8$ may be independently selected from the group consisting of hydrogen; halogen; hydroxyl; $C_1$-$C_6$ alkyl; phenyl; and naphthyl; or $R^7$ and $R^8$, together with the atoms to which they are attached, form a 4-6 membered heterocyclic or cycloalkyl ring; wherein $C_1$-$C_6$ alkyl, phenyl, naphthyl, the cycloalkyl ring, and the heterocyclic ring each may be substituted independently by one or more substituents selected from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; wherein R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In certain embodiments, L may be —O—(C$_1$-C$_{20}$ alkyl)-O—. In some instances, L may be —O—[(C$_1$-C$_6$ alkyl)-O]$_n$—, wherein n is 0, 1, 2, 3, 4, 5 or 6.

In some cases, at least one of $R^1$ and $R^2$ may be hydroxyl. In some embodiments, at least one of $R^1$ and $R^2$ may be $C_1$-$C_6$ alkyl.

In some embodiments, at least one of R5 and R6 may be —C1-C6 alkyl-Ar. In some instances, at least one of $R^5$ and $R^6$ may be —(CH$_2$)—Ar. In other instances, at least one of $R^5$ and $R^6$ may be -Q-phenyl. In certain embodiments, at least one of $R^5$ and $R^6$ may be hydrogen.

In an exemplary embodiment, a compound may be represented by:

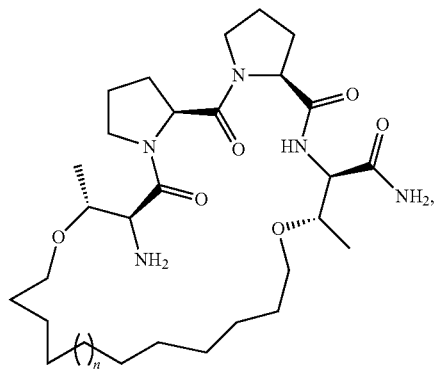

wherein n is an integer from 0-9.

In another exemplary embodiment, a compound may be represented by:

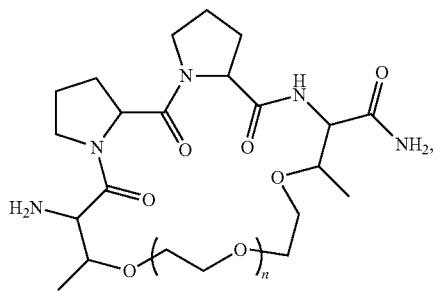

wherein n is an integer from 1-5.

In yet another exemplary embodiment, a compound may be represented by:

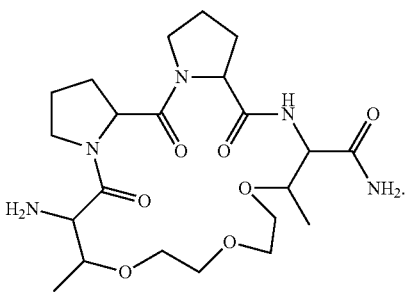 [SMILES: CC1OCCOCCOC(C)C(C(N)=O)NC(=O)C2CCCN2C(=O)C2CCCN2C(=O)C1N]

In still another exemplary embodiment, a compound may be represented by:

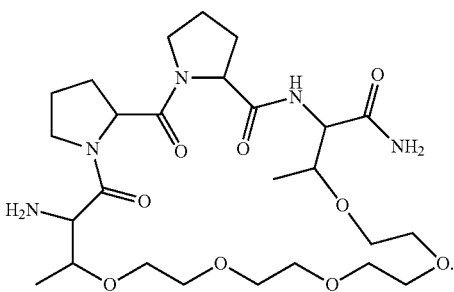 [SMILES: CC1OCCOCCOCCOCCOC(C)C(C(N)=O)NC(=O)C2CCCN2C(=O)C2CCCN2C(=O)C1N]

In some embodiments, disclosed compounds include those represented by the formula:

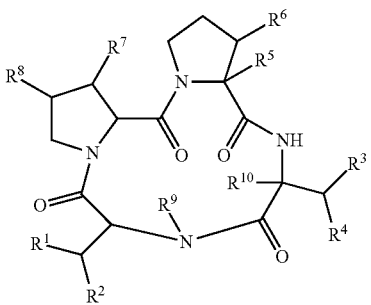

wherein:

$R^1$, $R^2$, $R^3$, and $R^4$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$SOR^x$; —$S(O)_2R^x$; —$NR^xC(O)R^x$; —$NR^xC(O)N(R^x)_2$; —$NR^xC(O)OR^x$; —$NR^xC(NR^x)N(R^x)_2$; and —$C(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ may be independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^9$ and $R^{10}$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(W)_2$; —$N(R^x)_2$; —$SOR^x$; —$S(O)_2R^x$; —$NR^xC(O)R^x$; —$NR^xC(O)N(R^x)_2$; —$NR^xC(O)OR^x$; —$NR^xC(NR^x)N(R^x)_2$; and —$C(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl; or $R^9$ and $R^{16}$ taken together with the atoms to which they are attached form a substituted or unsubstituted 4-6 membered ring; and pharmaceutically acceptable salts, stereoisomers, metabolites, and hydrates thereof.

In some embodiments, $R^1$, $R^2$, $R^3$, and $R^4$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$SOR^x$; —$S(O)_2R^x$; —$NR^xC(O)R^x$; —$NR^xC(O)N(R^x)_2$; —$NR^xC(O)OR^x$; —$NR^xC(NR^x)N(R^x)_2$; and —$C(R^x)_3$; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$ alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl- N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}N$—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

$R^f$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

$R^g$ may be selected, independently for each occurrence, from the group consisting of halogen, hydroxyl, —$NO_2$; —$N_3$; —CN; —SCN; $C_{1-6}$alkyl; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

$R^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$.

In some embodiments, $R^5$ and $R^6$ may be independently selected from the group consisting of -Q-Ar and hydrogen; wherein Q is independently selected from the group consisting of $C_{1-6}$alkoxy; $C_{1-6}$alkyl; $C_{2-6}$alkenyl; $C_{2-6}$alkynyl; $C_{3-6}$cycloalkyl; heterocyclyl; $C_{3-6}$cycloalkyl-$C_{1-6}$alkyl-; and heterocyclyl-$C_{1-6}$alkyl-; and a bond; and wherein Ar is selected from the group consisting substituted or unsubstituted phenyl or naphthyl, and substituted or unsubstituted heteroaryl; or $R^5$ and $R^6$, together with the atoms to which they are attached, form a substituted or unsubstituted 4-6 membered heterocyclic or cycloalkyl ring; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl and $C_{1-6}$alkoxy are each independently optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}N$—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

$R^f$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2; and $R^g$ may be selected, independently for each occurrence, from the group consisting of halogen, hydroxyl, —NO$_2$; —N$_3$; —CN; —SCN; C$_{1-6}$alkyl; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2.

In some cases, $R^7$ and $R^8$ may be independently selected from the group consisting of hydrogen; halogen; hydroxyl; C$_1$-C$_6$ alkyl; phenyl; and naphthyl; or $R^7$ and $R^8$, together with the atoms to which they are attached, form a 4-6 membered heterocyclic or cycloalkyl ring; wherein C$_1$-C$_6$ alkyl, phenyl, naphthyl, the cycloalkyl ring, and the heterocyclic ring each may be substituted independently by one or more substituents selected from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2; wherein R$^a$ and R$^{a'}$ may be selected, independently for each occurrence, from the group consisting of hydrogen and C$_{1-6}$alkyl, or R$^a$ and R$^{a'}$ when taken together with the nitrogen to which they are attached form a 4-6 membered heterocyclic ring, wherein C$_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In some embodiments, $R^9$ and $R^{10}$ may be independently selected from the group consisting of hydrogen; halogen; C$_{1-6}$alkyl; C$_{2-6}$alkenyl; C$_{2-6}$alkynyl; C$_{3-6}$cycloalkyl; phenyl; naphthyl; heteroaryl; heterocyclyl; C$_{3-6}$cycloalkyl-C$_{1-6}$alkyl-; phenyl-C$_{1-6}$alkyl-; naphthyl-C$_{1-6}$alkyl-; heteroaryl-C$_{1-6}$alkyl-; and heterocyclyl-C$_{1-6}$alkyl-; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein C$_{2-6}$alkenyl and C$_{2-6}$alkynyl, are each independently optionally substituted by one or more substituents each independently selected from R$^e$; wherein C$_{1-6}$alkyl is optionally substituted by one or more substituents each independently selected from R$^f$; wherein C$_{3-6}$cycloalkyl is independently optionally substituted by one or more substituents each independently selected from R$^g$;

$R^b$ may be selected, independently for each occurrence, from the group consisting of halogen; hydroxyl; —NO$_2$; —N$_3$; —CN; —SCN; C$_{1-6}$alkyl; C$_{2-6}$alkenyl; C$_{2-6}$alkynyl; C$_{3-6}$cycloalkyl; C$_{1-6}$alkoxy; C$_{3-6}$alkenyloxy; C$_{3-6}$alkynyloxy; C$_{3-6}$cycloalkoxy; C$_{1-6}$alkyl-S(O)$_w$, where w is 0, 1, or 2; C$_{1-6}$alkylC$_{3-6}$cycloalkyl-; C$_{3-6}$cycloalkyl-C$_{1-6}$alkyl-; C$_{1-6}$alkoxycarbonyl-N(R$^a$)—; C$_{1-6}$alkylN(R$^a$)—; C$_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and C$_{1-6}$alkyl-carbonyl-N(R$^a$)—;

R$^a$ and R$^{a'}$ may be selected, independently for each occurrence, from the group consisting of hydrogen and C$_{1-6}$alkyl, or R$^a$ and R$^{a'}$ when taken together with the nitrogen to which they are attached form a 4-6 membered heterocyclic ring, wherein C$_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —NO$_2$; —N$_3$; —CN; —SCN; oxo; C$_{1-6}$alkyl; C$_{2-6}$alkenyl; C$_{2-6}$alkynyl; C$_{3-6}$cycloalkyl; C$_{1-6}$alkoxy; C$_{3-6}$alkenyloxy; C$_{3-6}$alkynyloxy; C$_{3-6}$cycloalkoxy; C$_{1-6}$alkyl-S(O)$_w$, where w is 0, 1, or 2; C$_{1-6}$alkylC$_{3-6}$cycloalkyl-; C$_{3-6}$cycloalkyl-C$_{1-6}$alkyl-; C$_{1-6}$alkoxycarbonyl-N(R$^a$)—; C$_{1-6}$alkylN(R$^a$)—; C$_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and C$_{1-6}$alkyl-carbonyl-N(R$^a$)—;

$R^d$ may be selected, independently for each occurrence, from the group consisting of C$_{1-6}$alkyl, C$_{1-6}$alkylcarbonyl, and C$_{1-6}$alkylsulfonyl, wherein C$_{1-6}$alkyl is optionally substituted by one or more substituents each independently selected from halogen, hydroxyl, and R$^a$R$^{a'}$N—;

$R^e$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

$R^f$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

$R^g$ may be selected, independently for each occurrence, from the group consisting of halogen, hydroxyl, —NO$_2$; —N$_3$; —CN; —SCN; C$_{1-6}$alkyl; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

$R^x$ may be selected, independently, from the group consisting of hydrogen; halogen; C$_{1-6}$alkyl; C$_{2-6}$alkenyl; C$_{2-6}$alkynyl; C$_{3-6}$cycloalkyl; phenyl; naphthyl; heteroaryl; heterocyclyl; C$_{3-6}$cycloalkyl-C$_{1-6}$alkyl-; phenyl-C$_{1-6}$alkyl-; naphthyl-C$_{1-6}$alkyl-; heteroaryl-C$_{1-6}$alkyl-; and heterocyclyl-C$_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein C$_{2-6}$alkenyl and C$_{2-6}$alkynyl, are each independently optionally substituted by one or more substituents each independently selected from R$^e$; wherein C$_{1-6}$alkyl is optionally substituted by one or more substituents each independently selected from R$^f$; wherein C$_{3-6}$cycloalkyl is independently optionally substituted by one or more substituents each independently selected from R$^g$.

In some instances, $R^9$ may be hydrogen. In certain embodiments, $R^{10}$ may be hydrogen.

In some cases, at least one of $R^1$, $R^2$, $R^3$, and $R^4$ may be hydroxyl. In some instances, at least one of $R^1$, $R^2$, $R^3$, and $R^4$ may be $C_1$-$C_6$ alkyl.

In some embodiments, at least one of $R^5$ and $R^6$ may be —$C_1$-$C_6$ alkyl-Ar. In certain embodiments, at least one of $R^5$ and $R^6$ may be —($CH_2$)—Ar. In some cases, at least one of $R^5$ and $R^6$ may be -Q-phenyl. In some instances, at least one of $R^5$ and $R^6$ may be hydrogen.

In some embodiments, $R^9$ and $R^{10}$ taken together with the atoms to which they are attached may form a substituted or unsubstituted 4-6 membered ring. In certain embodiments, $R^9$ and $R^{10}$ taken together with the atoms to which they are attached may form a 4-membered ring.

In an exemplary embodiment, a compound may be represented by:

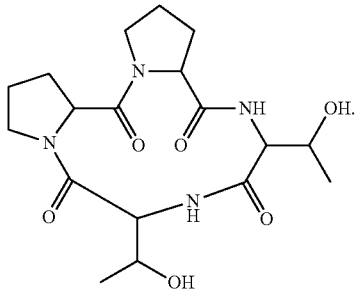 [SMILES: CC(O)C1NC(=O)C2CCCN2C(=O)C2CCCN2C(=O)C(C(C)O)NC1=O]

In another exemplary embodiment, a compound may be represented by:

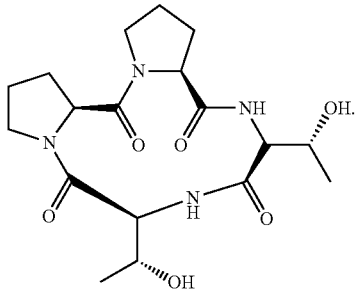

In yet another exemplary embodiment, a compound may be represented by:

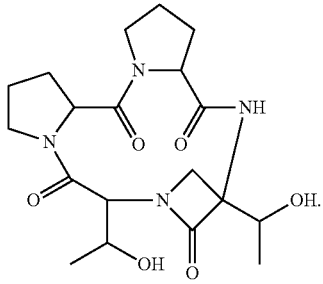 [SMILES: CC(O)C1C(=O)N2CCCC2C(=O)N2CCCC2C(=O)NC2(C(C)O)CN1C2=O]

In still another exemplary embodiment, a compound may be represented by:

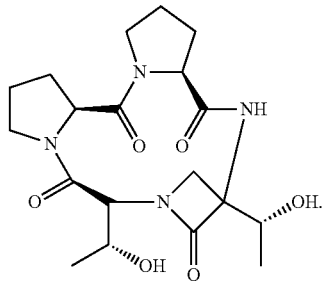

In some embodiments, disclosed compounds include those represented by the formula:

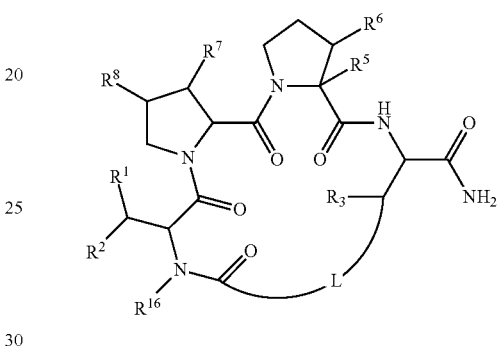

wherein:

$R^1$, $R^2$, and $R^3$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —C(O)$R^x$; —$CO_2(R^x)$; —C(O)N($R^x$)$_2$; —C($NR^x$)N($R^x$)$_2$; —OC(O)$R^x$; —$OCO_2R^x$; —OC(O)N($R^x$)$_2$; —N($R^x$)$_2$; —$SOR^x$; —S(O)$_2R^x$; —$NR^x$C(O)$R^x$; —$NR^x$C(O)N($R^x$)$_2$; —$NR^x$C(O)$OR^x$; —$NR^x$C($NR^x$)N($R^x$)$_2$; and —C($R^x$)$_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ may be independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^{16}$ may be selected from the group consisting of hydrogen; $C_1$-$C_6$ alkyl, optionally substituted by one or more substituents each independently selected from the group consisting of halogen, oxo, and hydroxyl; $C_{2-6}$alkenyl, optionally substituted by one or more substituents each independently selected from the group consisting of halogen, oxo, and hydroxyl; $C_{2-6}$alkynyl, optionally substituted by one or more substituents each independently selected from the group consisting of halogen, oxo, and hydroxyl; $C_{3-6}$cycloalkyl, optionally substituted by one or more substituents each independently selected from the group consisting of $C_{1-6}$alkyl, halogen, oxo, and hydroxyl; and phenyl, optionally substituted by one or more substituents each independently selected from the group consisting of $C_{1-6}$alkyl, $C_{1-6}$alkoxy; halogen, and hydroxyl; —C(O)R$^x$; —CO$_2$(R$^x$); —C(O)N(R$^x$)$_2$; —C(NR$^x$)N(R$^x$)$_2$; and —C(R$^x$)$_3$; wherein each occurrence of R$^x$ is independently selected from the group consisting of hydrogen; halogen; $C_{1-6}$alkyl; $C_{2-6}$alkenyl; $C_{2-6}$alkynyl; $C_{3-6}$cycloalkyl; and phenyl;

L may be selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted aryl; and substituted or unsubstituted heteroaryl; and pharmaceutically acceptable salts, stereoisomers, metabolites, and hydrates thereof.

In some embodiments, R$^1$, R$^2$, and R$^3$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$;

R$^b$ may be selected, independently for each occurrence, from the group consisting of halogen; hydroxyl; —NO$_2$; —N$_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkylC$_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

R$^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$, where w is 0, 1, or 2; $C_{1-6}$alkyl-$C_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and R$^a$R$^{a'}$N—;

R$^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; $C_{1-6}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; R$^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$.

In some embodiments, R$^5$ and R$^6$ may be independently selected from the group consisting of -Q-Ar and hydrogen; wherein Q is independently selected from the group consisting of $C_{1-6}$alkoxy; $C_{1-6}$alkyl; $C_{2-6}$alkenyl; $C_{2-6}$alkynyl; $C_{3-6}$cycloalkyl; heterocyclyl; $C_{3-6}$cycloalkyl-$C_{1-6}$alkyl-; and heterocyclyl-$C_{1-6}$alkyl-; and a bond; and wherein Ar is selected from the group consisting substituted or unsubstituted phenyl or naphthyl, and substituted or unsubstituted heteroaryl; or R$^5$ and R$^6$, together with the atoms to which they are attached, form a substituted or unsubstituted 4-6 membered heterocyclic or cycloalkyl ring; wherein heteroaryl is a 5-6 membered ring having one, two, or three heteroatoms each independently selected from N, O, or S;

wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl and $C_{1-6}$alkoxy are each independently optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}$N—; $R^aR^{a'}$N-carbonyl-; $R^aR^{a'}$N-carbonyl-N($R^a$)—; $R^aR^{a'}$N—$SO_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}$N—; $R^aR^{a'}$N-carbonyl-; $R^aR^{a'}$N-carbonyl-N($R^a$)—; $R^aR^{a'}$N—$SO_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}$N—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkylS(O)$_w$—, where w is 0, 1, or 2;

$R^f$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkylS(O)$_w$—, where w is 0, 1, or 2; and $R^g$ may be selected, independently for each occurrence, from the group consisting of halogen, hydroxyl, —$NO_2$; —$N_3$; —CN; $C_{1-6}$alkyl; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkylS(O)$_w$—, where w is 0, 1, or 2.

In some cases, $R^7$ and $R^8$ may be independently selected from the group consisting of hydrogen; halogen; hydroxyl; $C_1$-$C_6$ alkyl; phenyl; and naphthyl; or $R^7$ and $R^8$, together with the atoms to which they are attached, form a 4-6 membered heterocyclic or cycloalkyl ring; wherein $C_1$-$C_6$ alkyl, phenyl, naphthyl, the cycloalkyl ring, and the heterocyclic ring each may be substituted independently by one or more substituents selected from the group consisting of halogen; hydroxyl; —$NO_2$; —$N_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkylS(O)$_w$—, where w is 0, 1, or 2; wherein $R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In some embodiments, L may be —O—($C_1$-$C_{20}$ alkyl)-O—. In some instances, L may be —O—[($C_1$-$C_6$ alkyl)-O]$_n$—, where n is 0, 1, 2, 3, 4, 5 or 6.

In some cases, at least one of $R^1$ and $R^2$ may be hydroxyl. In some embodiments, at least one of $R^1$ and $R^2$ may be $C_1$-$C_6$ alkyl.

In certain embodiments, $R^5$ and $R^6$ may be hydrogen.

In some instances, $R^7$ and $R^8$ may be hydrogen.

In an exemplary embodiment, a compound may be represented by:

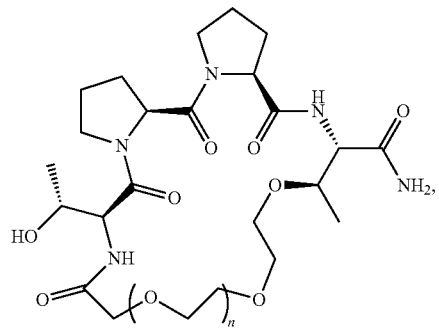

wherein n is 0, 1, 2, 3, 4 or 5.

In another exemplary embodiment, a compound may be represented by:

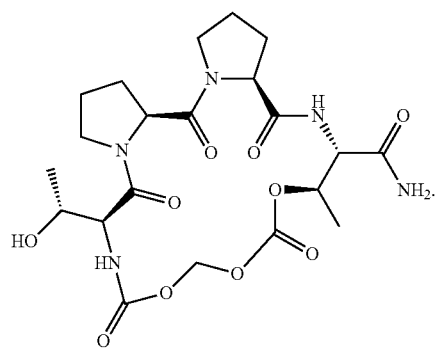 [SMILES: C[C@@H](O)[C@@H]1NC(=O)OCOC(=O)O[C@H](C)[C@@H](C(N)=O)NC(=O)[C@@H]2CCCN2C(=O)[C@@H]2CCCN2C1=O]

In yet another exemplary embodiment, a compound may be represented by:

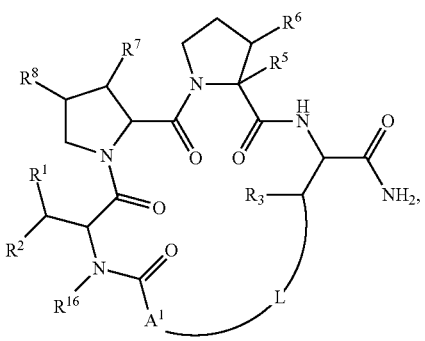

wherein:

$A^1$ is —($C_1$-$C_6$ alkyl)-aryl-.

In still another exemplary embodiment, a compound may be represented by:

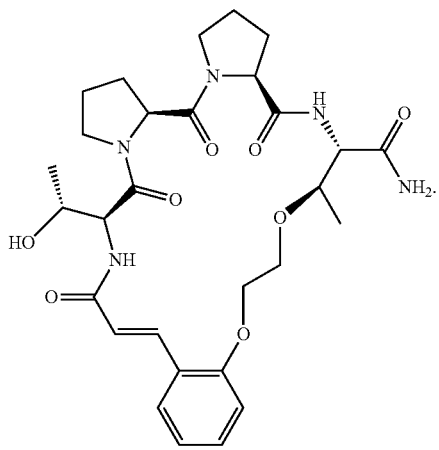 [SMILES: C[C@@H](O)[C@@H]1NC(=O)/C=C/c2ccccc2OCCO[C@H](C)[C@@H](C(N)=O)NC(=O)[C@@H]2CCCN2C(=O)[C@@H]2CCCN2C1=O]

In yet another exemplary embodiment, a compound may be represented by:

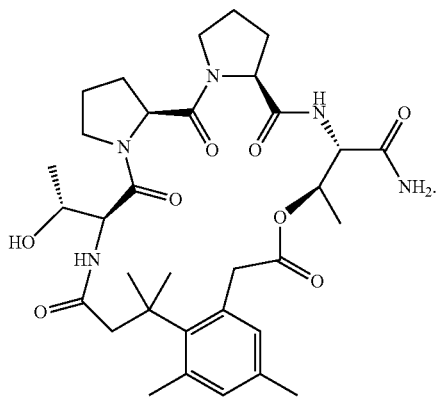 [SMILES: Cc1cc(C)c2c(c1)CC(=O)O[C@H](C)[C@@H](C(N)=O)NC(=O)[C@@H]1CCCN1C(=O)[C@@H]1CCCN1C(=O)[C@H]([C@@H](C)O)NC(=O)CC2(C)C]

In some embodiments, disclosed compounds include those represented by the formula:

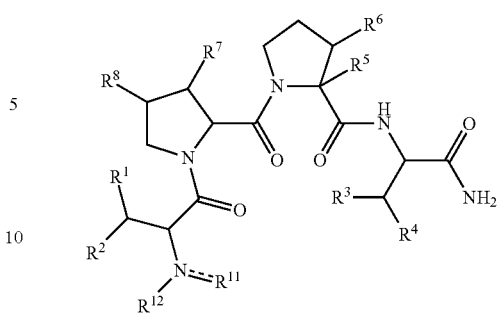

wherein:

$R^1$, $R^2$, $R^3$, and $R^4$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$SOR^x$; —$S(O)_2R^x$; —$NR^xC(O)R^x$; —$NR^xC(O)N(R^x)_2$; —$NR^xC(O)OR^x$; —$NR^xC(NR^x)N(R^x)_2$; and —$C(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ may be independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^{11}$ may be selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$C_1$-$C_6$ alkyl-phosphate; —$C(O)R^x$; —$CO_2(R^x)$; —$C(O)N(R^x)_2$; —$C(NR^x)N(R^x)_2$; —$N(R^x)_2$; —$NR^x(O)R^x$; —$NR^x(O)N(R^x)_2$; —$NR^xC(O)OR^x$; —$NR^x(NR^x)N(R^x)_2$; and —$C(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^{12}$ may be selected from the group consisting of hydrogen and substituted or unsubstituted $C_1$-$C_6$ alkyl; or $R^{12}$ is absent when $R^{11}$ forms a double bond with the N atom to which it is attached; and pharmaceutically acceptable salts, stereoisomers, metabolites, and hydrates thereof.

In some embodiments, $R^1$, $R^2$, $R^3$, and $R^4$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —$OR^x$; —$NO_2$; —$N_3$; —CN; —SCN; —$SR^x$; —$C(O)R^x$; —$CO_2(R^x)$; —$C(O)N(R^x)_2$; —$C(NR^x)N(R^x)_2$; —$OC(O)R^x$; —$OCO_2R^x$; —$OC(O)N(R^x)_2$; —$N(R^x)_2$; —$SOR^x$; —$S(O)_2R^x$; —$NR^x(O)R^x$; —$NR^x(O)N(R^x)_2$; —$NR^xC(O)OR^x$; —$NR^xC(NR^x)N(R^x)_2$; and —$C(R^x)_3$; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-$S(O)_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-$N(R^a)$—; $C_{1-6}$alkyl$N(R^a)$—; $C_{1-6}$alkyl-$N(R^a)$carbonyl-; $R^aR^{a'}$N—; $R^aR^{a'}$N-carbonyl-; $R^aR^{a'}$N-carbonyl-$N(R^a)$—; $R^aR^{a'}$N—$SO_2$—; and $C_{1-6}$alkyl-carbonyl-$N(R^a)$—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-$S(O)_w$—, where w is 0, 1, or 2; $C_{1-6}$alkyl-$C_{3-6}$cycloalkyl-; $C_{3-6}$cycloalkyl-$C_{1-6}$alkyl-; $C_{1-6}$alkoxycarbonyl-$N(R^a)$—; $C_{1-6}$alkyl$N(R^a)$—; $C_{1-6}$alkyl-$N(R^a)$carbonyl-; $R^aR^{a'}$N—; $R^aR^{a'}$N-carbonyl-; $R^aR^{a'}$N-carbonyl-$N(R^a)$—; $R^aR^{a'}$N—$SO_2$—; and $C_{1-6}$alkyl-carbonyl-$N(R^a)$—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}$N—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkyl$S(O)_w$—, where w is 0, 1, or 2;

$R^f$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkyl$S(O)_w$—, where w is 0, 1, or 2;

$R^g$ may be selected, independently for each occurrence, from the group consisting of halogen, hydroxyl, —$NO_2$; —$N_3$; —CN; —SCN; $C_{1-6}$alkyl; $C_{1-4}$alkoxy; $C_{1-4}$alkoxycarbonyl; $R^aR^{a'}$N—; $R^aR^{a'}$N-carbonyl; $R^aR^{a'}$N—$SO_2$—; and $C_{1-4}$alkyl$S(O)_w$—, where w is 0, 1, or 2;

$R^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$.

In some embodiments, $R^5$ and $R^6$ may be independently selected from the group consisting of -Q-Ar and hydrogen; wherein Q is independently selected from the group consisting of $C_{1-6}$alkoxy; $C_{1-6}$alkyl; $C_{2-6}$alkenyl; $C_{2-6}$alkynyl; $C_{3-6}$cycloalkyl; heterocyclyl; $C_{3-6}$cycloalkyl-$C_{1-6}$alkyl-; and heterocyclyl-$C_{1-6}$alkyl-; and a bond; and wherein Ar is selected from the group consisting substituted or unsubstituted phenyl or naphthyl, and substituted or unsubstituted heteroaryl; or $R^5$ and $R^6$, together with the atoms to which they are attached, form a substituted or unsubstituted 4-6 membered heterocyclic or cycloalkyl ring; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl and $C_{1-6}$alkoxy are each independently optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-$S(O)_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-$N(R^a)$—; $C_{1-6}$alkyl$N(R^a)$—; $C_{1-6}$alkyl- N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}N$—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

$R^f$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2; and $R^g$ may be selected, independently for each occurrence, from the group consisting of halogen, hydroxyl, —$NO_2$; —$N_3$; —CN; —SCN; $C_{1-6}$alkyl; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2.

In some cases, $R^7$ and $R^8$ may be independently selected from the group consisting of hydrogen; halogen; hydroxyl; $C_1$-$C_6$ alkyl; phenyl; and naphthyl; or $R^7$ and $R^8$, together with the atoms to which they are attached, form a 4-6 membered heterocyclic or cycloalkyl ring; wherein $C_1$-$C_6$ alkyl, phenyl, naphthyl, the cycloalkyl ring, and the heterocyclic ring each may be substituted independently by one or more substituents selected from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2; wherein $R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In some embodiments, $R^{11}$ may be selected from the group consisting of $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —$OR^x$; —$NO_2$; —$N_3$; —CN; —SCN; —$SR^x$; —C(O)$R^x$; —$CO_2(R^x)$; —C(O)N($R^x$)$_2$; —C($NR^x$)N($R^x$)$_2$; —OC(O)$R^x$; —$OCO_2R^x$; —OC(O)N($R^x$)$_2$; —N($R^x$)$_2$; —$SOR^x$; —S(O)$_2R^x$; —$NR^xC(O)R^x$; —$NR^xC(O)N(R^x)_2$; —$NR^xC(O)OR^x$; —$NR^xC(NR^x)N(R^x)_2$; and —C($R^x$)$_3$; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl-$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$— $SO_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —$NO_2$; —$N_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl-$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}N$—; $R^aR^{a'}N$-carbonyl-; $R^aR^{a'}N$-carbonyl-N($R^a$)—; $R^aR^{a'}N$—$SO_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}N$—;

$R^e$ may be selected, independently for each occurrence, from the group consisting of halogen; hydroxyl; —$NO_2$; —$N_3$; —CN; —SCN; $C_{1-4}$alkoxy; $C_{1-4}$alkoxycarbonyl; $R^aR^{a'}N$—; $R^aR^{a'}N$-carbonyl; $R^aR^{a'}N$—$SO_2$—; and $C_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^a$N—; R$^a$R$^a$N-carbonyl; R$^a$R$^a$N—SO$_2$—; and C$_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; C$_{1-6}$alkyl; C$_{1-4}$alkoxy; C$_{1-4}$alkoxycarbonyl; R$^a$R$^a$N—; R$^a$R$^a$N-carbonyl; R$^a$R$^a$N—SO$_2$—; and C$_{1-4}$alkylS(O)$_w$—, where w is 0, 1, or 2;

R$^x$ may be selected, independently, from the group consisting of hydrogen; halogen; C$_{1-6}$alkyl; C$_{2-6}$alkenyl; C$_{2-6}$alkynyl; C$_{3-6}$cycloalkyl; phenyl; naphthyl; heteroaryl; heterocyclyl; C$_{3-6}$cycloalkyl-C$_{1-6}$alkyl-; phenyl-C$_{1-6}$alkyl-; naphthyl-C$_{1-6}$alkyl-; heteroaryl-C$_{1-6}$alkyl-; and heterocyclyl-C$_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein C$_{2-6}$alkenyl and C$_{2-6}$alkynyl, are each independently optionally substituted by one or more substituents each independently selected from R$^e$; wherein C$_{1-6}$alkyl is optionally substituted by one or more substituents each independently selected from R$^f$; wherein C$_{3-6}$cycloalkyl is independently optionally substituted by one or more substituents each independently selected from R$^g$.

In some embodiments, R$^{11}$ may be an amino acid or peptide (e.g., a dipeptide, a tripeptide, or the like). In such instances, R$^{11}$ may be connected to the nitrogen to which it is attached though the C-terminus carboxyl group of the amino acid or peptide, i.e., by an amide linkage. In some embodiments, R$^{11}$ may be an amino acid selected from, but not limited to, alanine, cysteine, selenocysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine. The amino acid may be a D isomer, an L isomer, or a mixture of D and L isomers. In some cases, the amino acid may be modified. For example, in some embodiments, the terminal amine of the amino acid may be acylated (e.g., acetylated, benzoylated, 4-nitrobenzoylated, or the like), alkylated (e.g., methylated, ethylated, or C$_{1-6}$alkylated), benzylated, or sulfonylated (e.g., mesylated, tosylated or the like).

In an exemplary embodiment, a compound may be represented by:

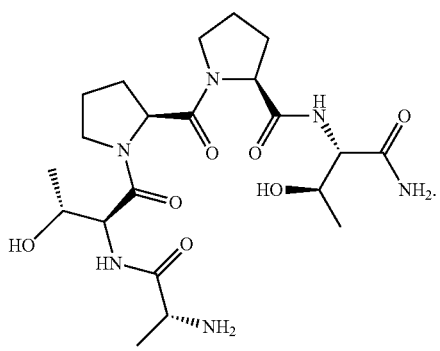 [SMILES: C[C@@H](N)C(=O)N[C@H](C(=O)N1CCC[C@H]1C(=O)N1CCC[C@H]1C(=O)N[C@H](C(N)=O)[C@@H](C)O)[C@@H](C)O]

In another exemplary embodiment, a compound may be represented by:

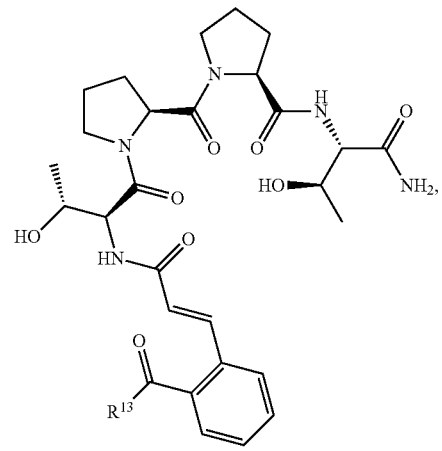

wherein R$^{13}$ may be selected from the group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^x$; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —NR$^x$C(O)R$^x$; —NR$^x$(O)N(R$^x$)$_2$; —NR$^x$C(O)OR$^x$; —NR$^x$(NR$^x$)N(R$^x$)$_2$; and —C(R$^x$)$_3$; wherein each occurrence of R$^x$ is independently selected from the group consisting of hydrogen; halogen; acyl; optionally substituted aliphatic; optionally substituted heteroaliphatic; optionally substituted aryl; and optionally substituted heteroaryl.

In some embodiments, R$^{13}$ may be selected from the group consisting of hydrogen, C$_{1-6}$alkyl; C$_{2-6}$alkenyl; C$_{2-6}$alkynyl; C$_{3-6}$cycloalkyl; phenyl; naphthyl; heteroaryl; heterocyclyl; C$_{3-6}$cycloalkyl-C$_{1-6}$alkyl-; phenyl-C$_{1-6}$alkyl-; naphthyl-C$_{1-6}$alkyl-; heteroaryl-C$_{1-6}$alkyl-; and heterocyclyl-C$_{1-6}$alkyl-; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$(O)R$^x$; —NR$^x$C(O)N(R$^x$)$_2$; —NR$^x$C(O)OR$^x$; —NR$^x$(NR$^x$)N(R$^x$)$_2$; and —C(R$^x$)$_3$; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein C$_{2-6}$alkenyl and C$_{2-6}$alkynyl, are each independently optionally substituted by one or more substituents each independently selected from R$^e$; wherein C$_{1-6}$alkyl is optionally substituted by one or more substituents each independently selected from R$^f$; wherein C$_{3-6}$cycloalkyl is independently optionally substituted by one or more substituents each independently selected from R$^g$;

R$^b$ may be selected, independently for each occurrence, from the group consisting of halogen; hydroxyl; —NO$_2$; —N$_3$; —CN; —SCN; C$_{1-6}$alkyl; C$_{2-6}$alkenyl; C$_{2-6}$alkynyl; C$_{3-6}$cycloalkyl; C$_{1-6}$ alkoxy; C$_{3-6}$alkenyloxy; C$_{3-6}$alkynyloxy; C$_{3-6}$cycloalkoxy; C$_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}$N—; $R^aR^{a'}$N-carbonyl-; $R^aR^{a'}$N-carbonyl-N($R^a$)—; $R^aR^{a'}$N—SO$_2$—; and $C_{1-6}$alkyl-carbonyl-N($R^a$)—;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl-$C_{3-6}$cycloalkyl-; $C_{3-6}$cycloalkyl-$C_{1-6}$alkyl-; $C_{1-6}$alkoxycarbonyl-N($R^a$)—; $C_{1-6}$alkylN($R^a$)—; $C_{1-6}$alkyl-N($R^a$)carbonyl-; $R^aR^{a'}$N—; $R^aR^{a'}$N-carbonyl-; $R^aR^{a'}$N-carbonyl-N($R^a$)—; $R^aR^{a'}$N—SO$_2$—; and $C_{1-6}$alkyl-carbonyl-N($R^a$)—;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}$N—;

$R^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—SO$_2$—; and $C_{1-4}$alkylS(O)$_w$—, where w is 0, 1, or 2;

$R^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; $R^aR^{a'}$N—; $R^aR^{a'}$N-carbonyl; $R^aR^{a'}$N—SO$_2$—; and $C_{1-4}$alkylS(O)$_w$—, where w is 0, 1, or 2;

$R^g$ may be selected, independently for each occurrence, from the group consisting of halogen, hydroxyl, —NO$_2$; —N$_3$; —CN; —SCN; $C_{1-6}$alkyl; $C_{1-4}$alkoxy; $C_{1-4}$alkoxycarbonyl; $R^aR^{a'}$N—; $R^aR^{a'}$N-carbonyl; $R^aR^{a'}$N—SO$_2$—; and $C_{1-4}$alkylS(O)$_w$—, where w is 0, 1, or 2;

$R^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$.

In an exemplary embodiment, a compound may be represented by:

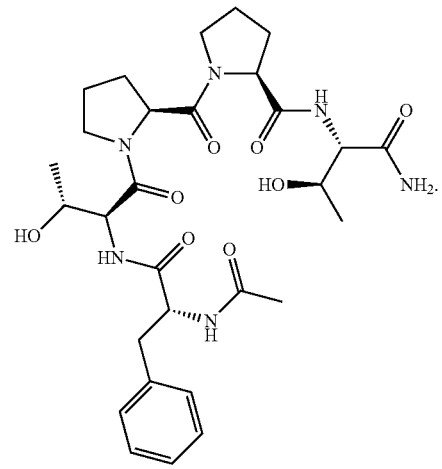 [SMILES: CC(=O)N[C@H](Cc1ccccc1)C(=O)N[C@H](C(=O)N1CCC[C@H]1C(=O)N1CCC[C@H]1C(=O)N[C@H](C(N)=O)[C@@H](C)O)[C@@H](C)O]

In another exemplary embodiment, a compound may be represented by:

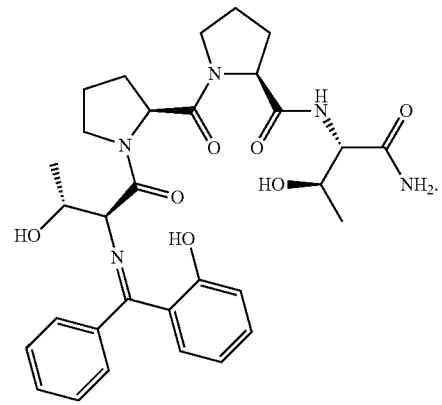 [SMILES: C[C@@H](O)[C@H](N=C(c1ccccc1)c1ccccc1O)C(=O)N1CCC[C@H]1C(=O)N1CCC[C@H]1C(=O)N[C@H](C(N)=O)[C@@H](C)O]

In yet another exemplary embodiment, a compound may be represented by:

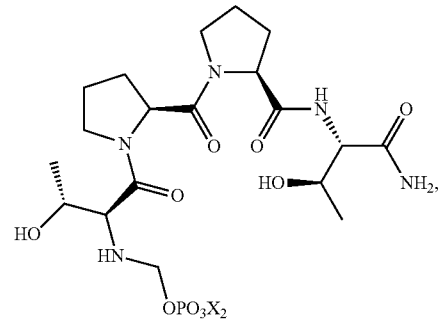

wherein $X_2$ is a divalent cation or is selected from the group consisting of hydrogen, a monovalent cation, a pair of electrons, or a combination thereof.

In still another exemplary embodiment, a compound may be represented by:

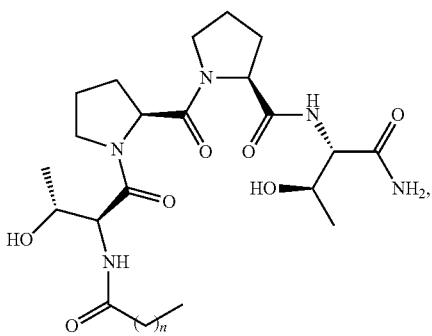

wherein n is an integer from 1-20.

In some embodiments, n may be 1, 2, 3, 4, 5, 6, 7, 8, 9, 10, 11, 12, 13, 14, 15, 16, 17, 18, 19, or 20. In certain embodiments, n may be 10. In another embodiment, n may be 15. In yet another embodiment, n may be 17.

In yet another exemplary embodiment, a compound may be represented by:

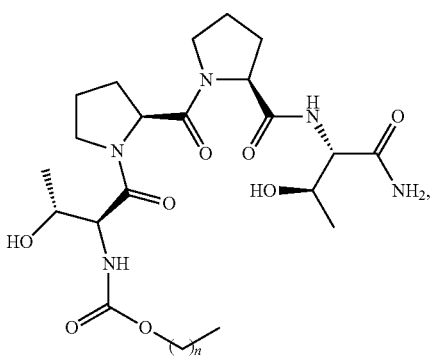

wherein n is an integer from 1-20.

In some embodiments, n may be 1, 2, 3, 4, 5, 6, 7, 8, 9, 10, 11, 12, 13, 14, 15, 16, 17, 18, 19, or 20. In another embodiment, n may be 15.

In still another exemplary embodiment, a compound may be represented by:

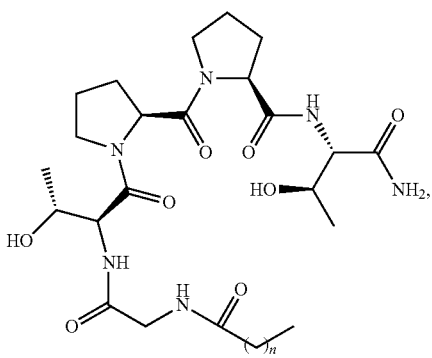

wherein n is an integer from 1-20.

In some embodiments, n may be 1, 2, 3, 4, 5, 6, 7, 8, 9, 10, 11, 12, 13, 14, 15, 16, 17, 18, 19, or 20. In another embodiment, n may be 13.

In yet another exemplary embodiment, a compound may be represented by:

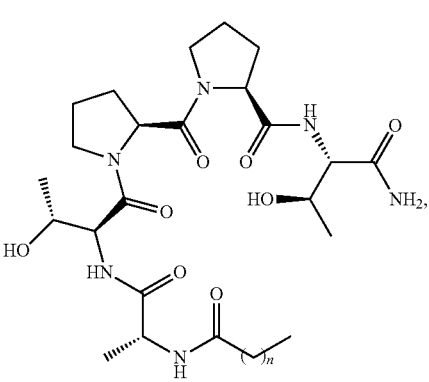

wherein n is an integer from 1-20.

In some embodiments, n may be 1, 2, 3, 4, 5, 6, 7, 8, 9, 10, 11, 12, 13, 14, 15, 16, 17, 18, 19, or 20. In another embodiment, n may be 13.

In some embodiments, disclosed compounds include those represented by the formula:

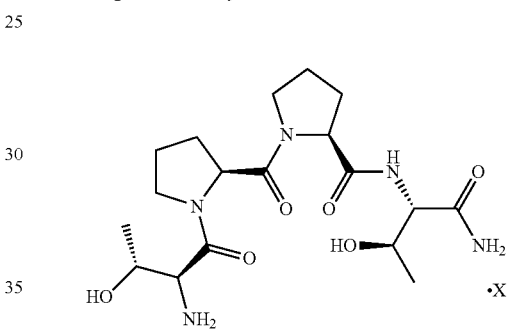

wherein X may be selected from the group consisting of:

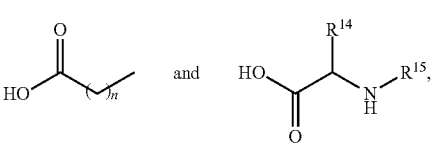

wherein:

n may be an integer from 8-20;

$R^{14}$ is selected from the group consisting of hydrogen; $C_1$-$C_6$ alkyl; —($C_1$-$C_6$ alkyl)-phenyl; —($C_1$-$C_6$ alkyl)-phenol; —($C_1$-$C_6$ alkyl)-heteroaryl; —($C_1$-$C_6$ alkyl)-SH; —($C_1$-$C_6$ alkyl)-S—($C_1$-$C_6$ alkyl); —($C_1$-$C_6$ alkyl)-OH; —($C_1$-$C_6$ alkyl)-O—($C_1$-$C_6$ alkyl); —($C_1$-$C_6$ alkyl)-NH$_2$; —($C_1$-$C_6$ alkyl)-NH—($C_1$-$C_6$ alkyl); —($C_1$-$C_6$ alkyl)-guanidine; —($C_1$-$C_6$ alkyl)-C(O)OH; —($C_1$-$C_6$ alkyl)-C(O)O—($C_1$-$C_6$ alkyl); —($C_1$-$C_6$ alkyl)-C(O)NH$_2$;

$R^{15}$ is selected from the group consisting of acyl, alkylsulfonyl, and arylsulfonyl;

$R^{18}$ is hydrogen, or $R^{14}$ and $R^{18}$ together with the atoms to which they are attached form a 4-7 membered ring; and stereoisomers, metabolites, and hydrates thereof.

In an exemplary embodiment, a compound may be represented by:

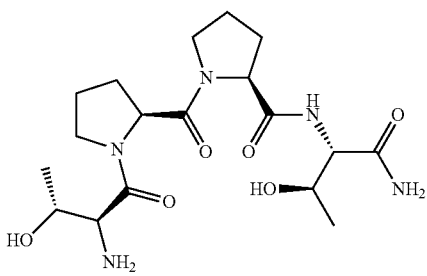 [SMILES: C[C@@H](O)[C@H](N)C(=O)N1CCC[C@H]1C(=O)N1CCC[C@H]1C(=O)N[C@H](C(N)=O)[C@@H](C)O]

and a second compound complexed with the first, wherein the second compound may be selected from the group consisting of:

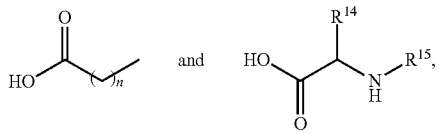

wherein:

n may be an integer from 8-20;

$R^{14}$ is selected from the group consisting of hydrogen; $C_1$-$C_6$ alkyl; —($C_1$-$C_6$ alkyl)-phenyl; —($C_1$-$C_6$ alkyl)-phenol; —($C_1$-$C_6$ alkyl)-heteroaryl; —($C_1$-$C_6$ alkyl)-SH; —($C_1$-$C_6$ alkyl)-S—($C_1$-$C_6$ alkyl); —($C_1$-$C_6$ alkyl)-OH; —($C_1$-$C_6$ alkyl)-O—($C_1$-$C_6$ alkyl); —($C_1$-$C_6$ alkyl)-NH$_2$; —($C_1$-$C_6$ alkyl)-NH—($C_1$-$C_6$ alkyl); —($C_1$-$C_6$ alkyl)-guanidine; —($C_1$-$C_6$ alkyl)-C(O)OH; —($C_1$-$C_6$ alkyl)-C(O)O—($C_1$-$C_6$ alkyl); —($C_1$-$C_6$ alkyl)-C(O)NH$_2$;

$R^{15}$ is selected from the group consisting of acyl, alkylsulfonyl, and arylsulfonyl;

$R^{18}$ is hydrogen, or $R^{14}$ and $R^{18}$ together with the atoms to which they are attached form a 4-7 membered ring; and stereoisomers, metabolites, and hydrates thereof.

In some embodiments, acyl may be selected from the group consisting of acetyl, benozyl, and 4-nitrobenzoyl.

In certain embodiments, arylsulfonyl may be toluenesulfonyl.

In some instances, $R^{14}$ may be selected from the group consisting of hydrogen, 2-butanyl, and benzyl.

In some embodiments, n may be 8, 9, 10, 11, 12, 13, 14, 15, 16, 17, 18, 19, or 20. In another embodiment, n may be selected from the group consisting of 14 and 16.

In some embodiments, the counterion may be an amino acid or peptide (e.g., a dipeptide, a tripeptide, or the like). For example, in some embodiments, the counterion may be an amino acid selected from, but not limited to, alanine, cysteine, selenocysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine. The amino acid may be a D isomer, an L isomer, or a mixture of D and L isomers. Generally, the amine of the amino acid is modified. For example, the N-terminal amino group may be acylated (e.g., acetylated, benozylated, 4-nitrobenzoylated, or the like) or sulfonylated (e.g., mesylated, tosylated, or the like).

In certain embodiments, the counterion may be selected from the group consisting of:

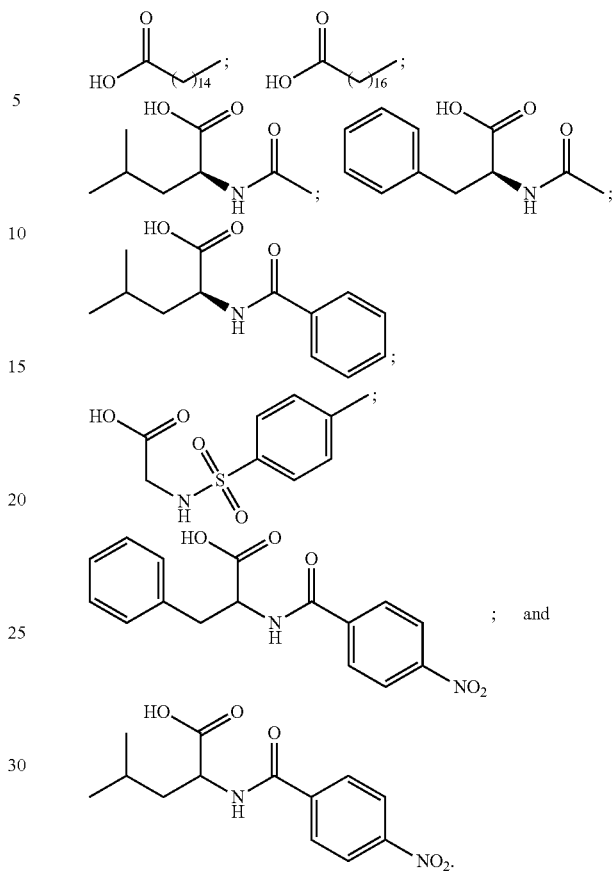

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or 5) may possess enhanced therapeutic characteristic relative to racemic formulations of a disclosed compounds or mixture of compounds.

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists. For example, disclosed compounds may possess a 10-fold to 20-fold enhanced potency compared to GLYX-13. GLYX-13 is represented by:

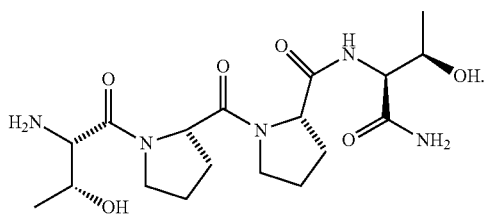

For example, provided herein are compounds that may be at least about 20-fold more potent as compared to GLYX-13, as measured by burst activated NMDA receptor-gated single neuron conductance ($I_{NMDA}$) in a culture of hippocampal CA1 pyramidal neurons at a concentration of 50 nM. In another embodiment, a provided compound may be capable of generating an enhanced single shock evoked NMDA receptor-gated single neuron conductance ($I_{NMDA}$) in hippocampal CA1 pyramidal neurons at concentrations of 100 nM to 1 µM. Disclosed compounds may have enhanced potency as compared to GLYX-13 as measured by magnitude of long term potentiation (LTP) at Schaffer collateral-CA-1 synapses in in vitro hippocampal slices.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=($TD_{50}$):($ED_{50}$). In some embodiments, a disclosed compound may have a therapeutic index of at least about 10:1, at least about 50:1, at least about 100:1, at least about 200:1, at least about 500:1, or at least about 1000:1.

The compounds described above may exhibit one or more advantageous properties over GLYX-13. For example, the compounds may be more stable than GLYX-13. For instance, in some embodiments, the compounds may have enhanced proteolytic stability, which may prevent or lower the rate of hydrolysis of one or more amide bonds in the compounds. In some embodiments, the cyclic compounds described above may be more proteolytically stable than GLYX-13. The enhanced stability of the compounds may be advantageous, for example, for prolonging the storage life of the compounds. The enhanced stability may also be beneficial for oral administration of the compounds. In some embodiments, the compounds may have enhanced oral bioavailability relative to GLYX-13.

In some embodiments, the cyclic compounds described above may be resistant to hydrolysis by peptide enzymes, may be bioreversible for esterase activity, and/or may have increased lipophilicity relative to GLYX-13.

In certain embodiments, the compounds contemplated above may be prodrugs. That is, the compounds may be inactive or less active prior to metabolism in vivo into an active agent. In some instances, the compounds may hydrolyze to form the active agent. For example, hydrolysis may occur at a terminal amide bond, a terminal ester bond, a terminal carbamate bond, and/or a terminal carbonate bond.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound. Methods Methods for treating cognitive disorders and for enhancing learning are provided. Such methods include administering a pharmaceutically acceptable formulation of one or more of the disclosed compounds to a patient in need thereof. Also contemplated are methods of treating patients suffering from, memory deficits associated with aging, schizophrenia, special learning disorders, seizures, post-stroke convulsions, brain ischemia, hypoglycemia, cardiac arrest, epilepsy, migraine, as well as Huntington's, Parkinson's and Alzheimer's disease.

Other methods contemplated include the treatment of cerebral ischemia, stroke, brain trauma, brain tumors, acute neuropathic pain, chronic neuropathic pain, sleep disorders, drug addiction, depression, certain vision disorders, ethanol withdrawal, anxiety, memory and learning disabilities, autism, epilepsy, AIDS dementia, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, impulse control disorders, Alzheimer's disease, memory loss that accompanies early stage Alzheimer's disease, attention deficit disorder, ADHD, schizophrenia, amelioration of opiate, nicotine addiction, ethanol addition, traumatic brain injury, spinal cord injury, post-traumatic stress syndrome, and Huntington's chorea.

In yet another aspect, a method for enhancing pain relief and for providing analgesia to an animal is provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present.

Disorganized type schizophrenia may be characterized where thought disorder and flat affect are present together.

Catatonic type schizophrenia may be characterized where the subject may be almost immobile or exhibit agitated, purposeless movement. Symptoms can include catatonic stupor and waxy flexibility.

Undifferentiated type schizophrenia may be characterized where psychotic symptoms are present but the criteria for paranoid, disorganized, or catatonic types have not been met.

Residual type schizophrenia may be characterized where positive symptoms are present at a low intensity only.

Post-schizophrenic depression may be characterized where a depressive episode arises in the aftermath of a schizophrenic illness where some low-level schizophrenic symptoms may still be present.

Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis.

In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

Additionally, methods are provided for treating obsessive-compulsive disorder (OCD).

EXAMPLES

The following examples are provided for illustrative purposes only, and are not intended to limit the scope of the disclosure.

Example 1—Preparation of GLYX-13 Palmitic Acid Complex (NRX-3001)

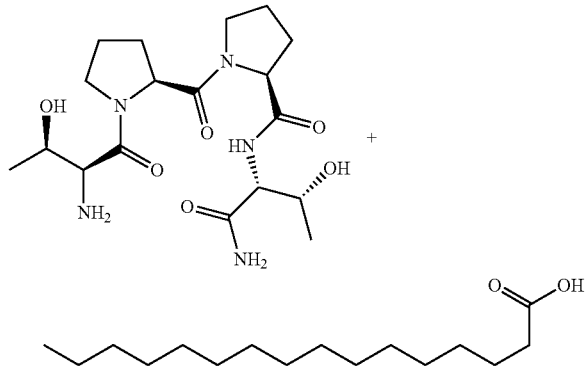

Scheme A. Complexation of GLYX-13 and Palmitic Acid.

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | Palmitic acid | 76.8 | mg | 256.24 | 3 mmol | 3 |

| | | | | | | |
|---|---|---|---|---|---|---|
| 3 | MeOH | 5 | mL | — | — | — |
| 4 | Diethyl ether | 10 | mL | — | — | — |

GLYX-13 (41.3 mg, 1 mmol) and Palmitic acid (76.8 mg, 3 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 50-60° C. The solid compound was analyzed by $^1$H NMR, HPLC, PXRD, DSC and TGA.

Example 2—Preparation of GLYX-13 N-p-tosylglycine Complex (NRX-3002)

Scheme B. Complexation of GLYX-13 and N-p-tosylglycine.

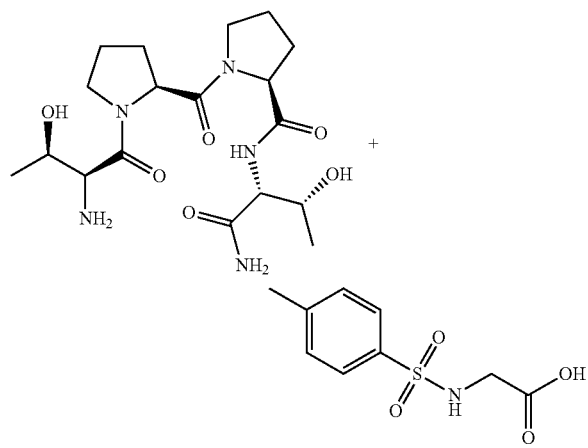

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | N-P-Tosylglycine | 22.9 | mg | 229.25 | 1 mmol | 1 |
| 3 | MeOH | 5 | mL | — | — | — |
| 4 | Diethyl ether | 10 | mL | — | — | — |

GLYX-13 (41.3 mg, 1 mmol) and N-P-Tosylglycine (22.9 mg, 1 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 90-110° C. The solid compound was analyzed by IR, $^1$H NMR, HPLC, PXRD, DSC and TGA.

Example 3—Preparation of GLYX-13 Stearic Acid Complex (NRX-3003)

Scheme C. Complexation of GLYX-13 and Stearic Acid.

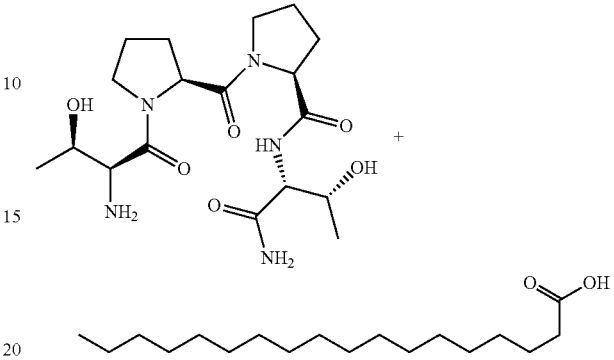

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | Stearic acid | 85.2 | mg | 284.48 | 3 mmol | 3 |
| 3 | MeOH | 5 | mL | — | — | — |
| 4 | Diethyl ether | 10 | mL | — | — | — |

GLYX-13 (41.3 mg, 1 mmol) and Stearic acid (85.2 mg, 3 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 55-90° C. The solid compound was analyzed by IR, $^1$H NMR, HPLC, PXRD, DSC and TGA.

Example 4—Preparation of GLYX-13 N-acetyl-L-phenylalanine Complex (NRX-3004)

Scheme D. Complexation of GLYX-13 and N-acetyl-L-phenylalanine.

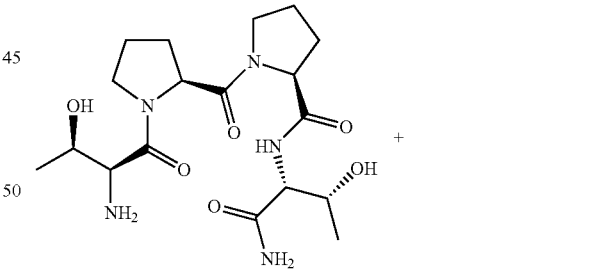

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | N-acetyl-L-phenylalanine | 41.4 | mg | 207.23 | 2 mmol | 2 |
| 3 | MeOH | 5 | mL | — | — | — |
| 4 | Diethyl ether | 10 | mL | — | — | — |

GLYX-13 (41.3 mg, 1 mmol) and N-acetyl-L-phenylalanine (41.4 mg, 2 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 90-120° C. The solid compound was analyzed by IR, $^1$H NMR, HPLC, PXRD, DSC and TGA.

$^1$H NMR: (400 MHz, DMSO): FIG. 1 shows the $^1$H NMR spectrum for NRX-3004.

Figure 2:
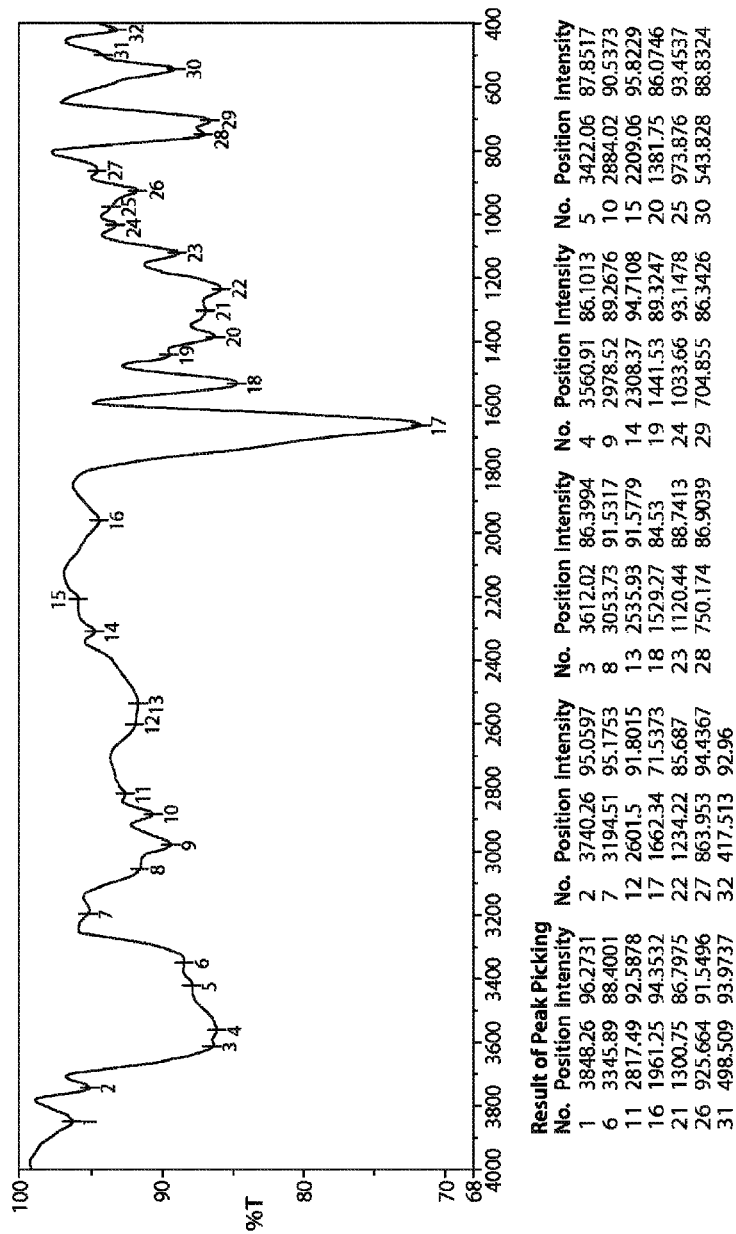
FIG. 2 shows an IR spectrum for NRX-3004.

IR: FIG. 2 shows the IR spectrum for NRX-3004.

Example 5—Preparation of GLYX-13 N-acetyl-L-leucine Complex (NRX-3005)

Scheme E. Complexation of GLYX-13 and N-acetyl-L-leucine.

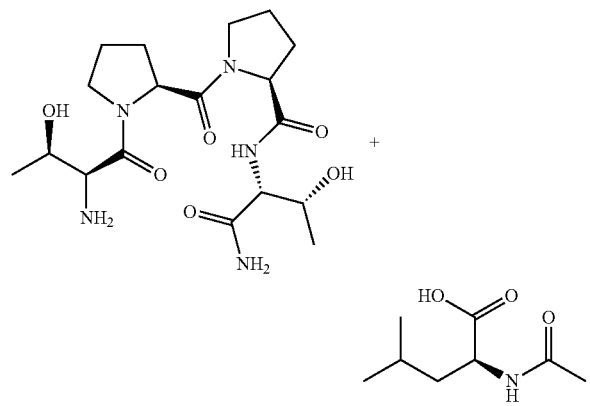

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | N-Acetyl-L-leucine | 34.6 | mg | 173.21 | 2 mmol | 2 |
| 3 | MeOH | 5 | mL | — | — | — |
| 4 | Diethyl ether | 10 | mL | — | — | — |

GLYX-13 (41.3 mg, 1 mmol) and N-Acetyl-L-leucine (34.6 mg, 2 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 90-110° C. The solid compound was analyzed by IR, $^1$H NMR, HPLC, PXRD, DSC and TGA.

Example 6—Preparation of GLYX-13 N-benzoyl-L-leucine Complex (NRX-3006)

Scheme F. Complexation of GLYX-13 and N-benzoyl-L-leucine.

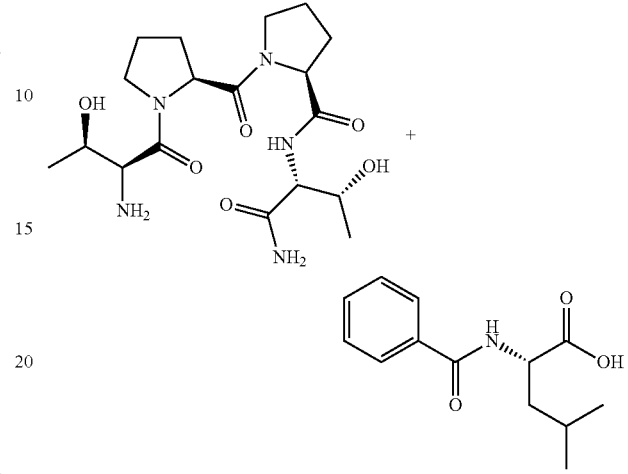

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | N-Benzoyl-L-leucine | 23.5 | mg | 235.28 | 1 mmol | 1 |
| 3 | MeOH | 5 | mL | — | — | — |
| 4 | Diethyl ether | 10 | mL | — | — | — |

GLYX-13 (41.3 mg, 1 mmol) and N-Benzoyl-L-leucine (23.5 mg, 1 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 90-110° C. The solid compound was analyzed by IR, $^1$H NMR, HPLC, PXRD, DSC and TGA.

Example 7—Preparation of GLYX-13—2-(4-nitrobenzamido)-3-phenylpropanoic acid Complex (NRX-3007)

Scheme G. Complexation of GLYX-13 and 2-(4-nitrobenzamido)-3-phenylpropanoic acid.

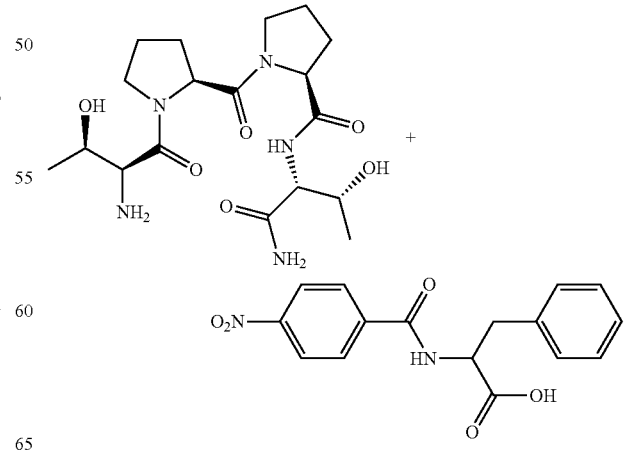

| S.No | Raw Material | Qty. | Unit | M.W. | Moles | Ratio |
|---|---|---|---|---|---|---|
| 1 | GLYX-13 | 41.3 | mg | 413.23 | 1 mmol | 1 |
| 2 | 2-(4-Nitrobenzamido)-3-phenylpropanoic acid | 31.4 | mg | 314.09 | 1 mmol | 1 |
| 3 | MeOH | 5 | mL | — | — | — |
| 4 | Diethyl ether | 10 | mL | — | — | — |

GLYX-13 (41.3 mg, 1 mmol) and 2-(4-nitrobenzamido)-3-phenylpropanoic acid (31.4 mg, 1 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 90-110° C. The solid compound was analyzed by IR, $^1$H NMR, HPLC, PXRD, DSC and TGA.

Example 8—Preparation of GLYX-13—4-methyl-2-(4-nitrobenzamido)-pentanoic acid Complex (NRX-3008)

Scheme H. Complexation of GLYX-13 and 4-methyl-2-(4-nitrobenzamido)-pentanoic acid.

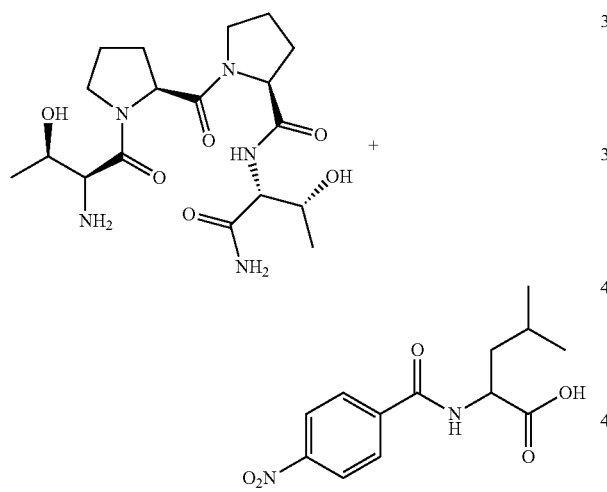

| S.No | Raw Material | Qty. | Unit | M.W. | Moles | Mole Ratio |
|---|---|---|---|---|---|---|
| 1 | GLYX-13 | 41.3 | mg | 413.23 | 1 mmol | 1 |
| 2 | 4-Methyl-2-(4-nitrobenzamido)pentanoic acid | 28 | mg | 280.11 | 1 mmol | 1 |
| 3 | MeOH | 5 | mL | — | — | — |
| 4 | Diethyl ether | 10 | mL | — | — | — |

GLYX-13 (41.3 mg, 1 mmol) and 4-Methyl-2-(4-nitrobenzamido) pentanoic acid (28 mg, 1 mmol) in MeOH (5 mL) were stirred in a RB flask for 30 minutes at room temperature. Methanol was removed at room temperature and then diethyl ether was added to the crude compound. The crude compound in diethyl ether was stirred at room temperature for 15 minutes. The organic solvent was distilled off to get the free flowing solid having melting point 80-110° C. The solid compound was analyzed by IR, $^1$H NMR, HPLC, PXRD, DSC and TGA.

Figure 3:
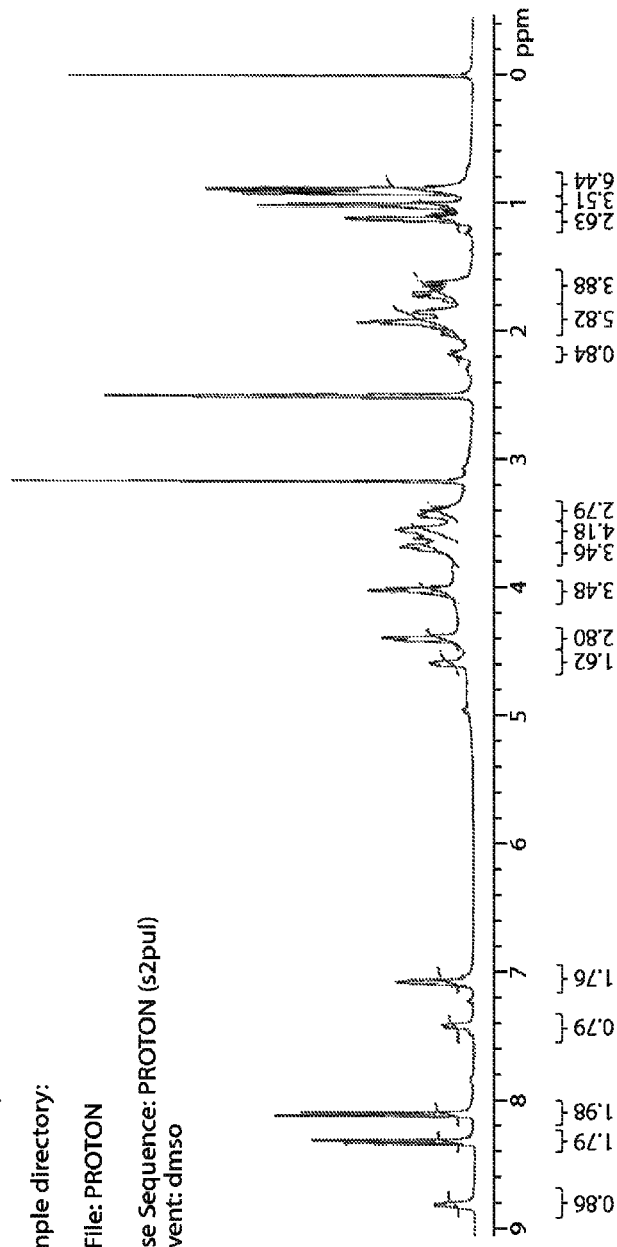
FIG. 3 shows a $^1$H NMR spectrum for NRX-3008.

$^1$H NMR: (400 MHz, DMSO): FIG. 3 shows the $^1$H NMR spectrum for NRX-3008.

Example 9—Preparation of GLYX-13 Coupled to Palmitic Acid (NRX-7005)

Scheme I. Synthesis of NRX-7005.

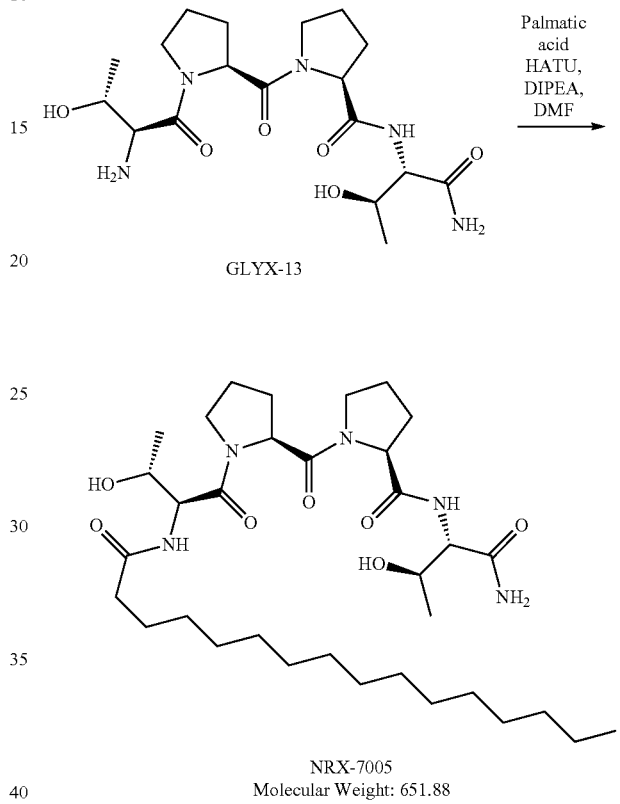

NRX-7005
Molecular Weight: 651.88

GLYX-13 (58 mg, 1.4 mmol), palmitic acid (30 mg, 1.17 mmol), and DIPEA (45.7 mg, 3.5 mmol) were dissolved in DMF (5 mL) and cooled to 0° C. HATU (111 mg, 2.93 mmol) was added to the above reaction mixture at 0° C. The reaction mixture was stirred at rt for 12 h. After the completion of starting materials, the reaction mixture was diluted with water (2×5 mL). The aqueous layer was extracted with ethyl acetate (2×25 mL), washed with brine solution (25 mL) and dried over anhydrous $Na_2SO_4$. Evaporation of the solvent furnished the crude product, which was purified by column chromatography (100-200 mesh silica gel, 20% EtOAc in hexane) to yield 20 mg of the palmitic acid coupled GLYX-13 NRX-7005 as a gummy solid.

Figure 4:
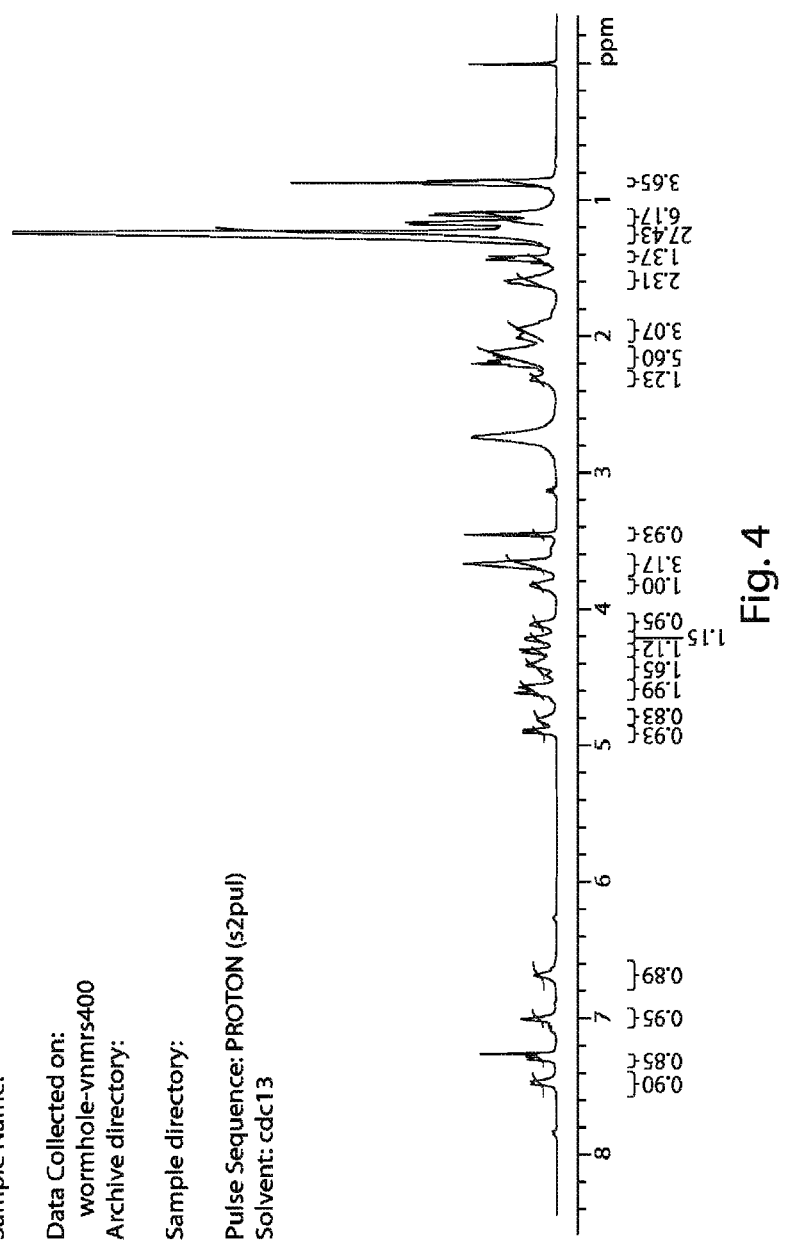
FIG. 4 shows a $^1$H NMR spectrum for NRX-7005.

$^1$H NMR: (400 MHz, $CDCl_3$): FIG. 4 shows the $^1$H NMR spectrum for NRX-7005.

Mass m/z: 652.5 [M$^+$+1].

Example 10—Preparation of GLYX-13 Coupled to 2-hydroxybenzophenone (NRX-7001)

Scheme J. Synthesis of NRX-7001.

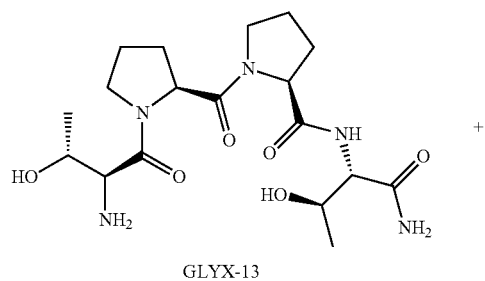

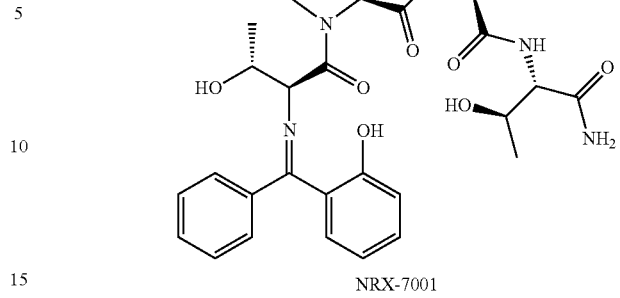

To a stirred solution of GLYX-13 (110 mg, 0.26 mmol) in DMF (4 mL), diisopropyl ethyl amine (DIPEA) (100 μL) and 2-hydroxybenzophenone (105 mg, 0.53 mmol) were added and stirred at room temperature for 48 h. After completion of the reaction the volatiles were evaporated under reduced pressure to furnish the crude product which was purified by preparative HPLC to furnish NRX-7001 (50 mg, 32%).

$^1$H NMR: (400 MHz, CDCl$_3$): δ 7.71 (d, 1H), 7.51 (d, 4H), 7.28-7.18 (m, 6H), 6.98 (d, 1H), 6.82 (d, 1H), 6.76 (d, 1H), 6.66-6.61 (m, 1H), 5.90 (d, 1H), 4.58 (t, 2H), 4.44 (t, 4H), 4.37-4.30 (m, 2H), 4.09 (q, 2H), 3.92 (m, 1H), 3.82-3.54 (m, 5H), 3.50-3.41 (m, 2H), 2.85-2.81 (m, 1H), 1.62 (m, 5H), 1.39-1.22 (m, 6H).

Mass m/z: 594.3 [M$^+$+1].

Example 11—Preparation of NRX-7018

Scheme K. Synthesis of NRX-7018.

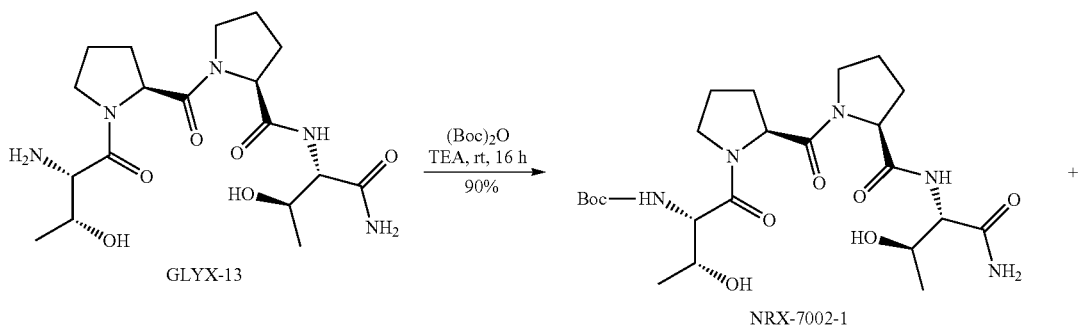

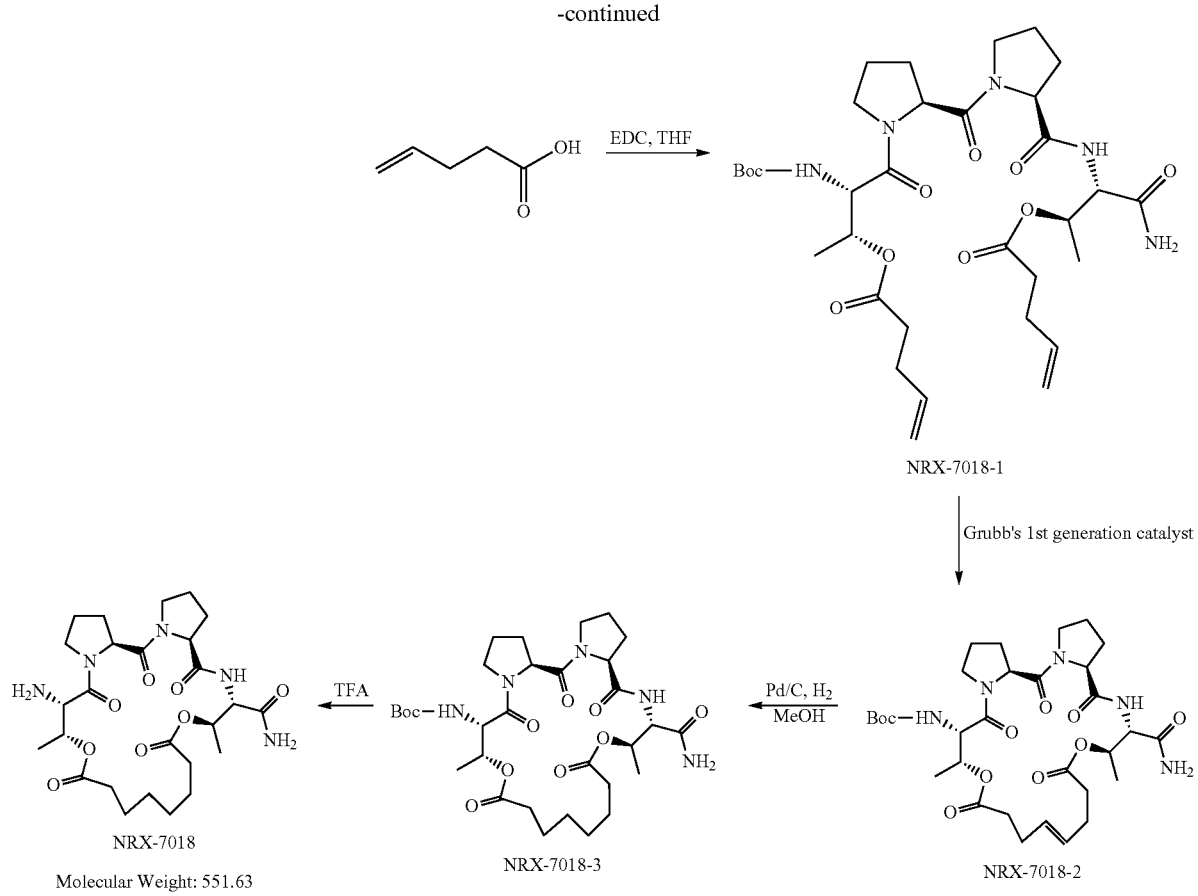

Synthesis of NRX-7002-1

To a solution of GLYX-13 (100 mg, 0.24 mmol) in 1,4-dioxane (5 mL), (Boc)₂O (0.08 mL, 0.36 mmol) and TEA (0.06 mL, 0.48 mmol) were added and stirred for 16 h at room temperature. After completion of the starting materials as indicated by TLC, volatiles were evaporated under reduced pressure, which up on trituration with n-Hexanes furnished NRX-7002-1 (110 mg, 90%) as a white solid.

Synthesis of NRX-7018-1

To a stirred solution of NRX-7002-1 (250 mg, 0.487 mmol) in THF (8 mL), 4-pentenoic acid (146 mg, 0.16 mL, 1.46 mmol) was added at ambient temperature. To the same reaction mixture, diisopropylethylamine (0.5 mL, 2.92 mmol) followed by EDC.HCl (372 mg, 1.949 mmol) and a catalytic amount of DMAP were added and stirring continued overnight. The volatiles were removed under reduced pressure, the residue was dissolved in ethyl acetate (25 mL) and washed with water (2×10 mL), 5% aqueous citric acid solution (2×10 mL), 5% sodium bicarbonate solution (1×15 mL) and brine (10 mL). The organic layer was dried over anhydrous sodium sulphate and concentrated in vacuo to afford NRX-7018-1 (290 mg, yield 87%) as a white solid.

Synthesis of NRX-7018-2

To a stirred solution of NRX-7018-1 (200 mg, 0.295 mmol) in DCM (600 mL), 1$^{st}$ generation Grubb's (5 mol %) catalyst was added at ambient temperature. The reaction mixture was stirred at ambient temperature for 3 days. After completion of the reaction, DCM was concentrated to 30 mL, filtered through a celite pad, and washed with DCM (30 mL). The filtrates were concentrated to afford a crude reaction mixture. The crude compound was purified by column chromatography using 5% methanol in DCM as eluent to afford NRX-7018-2 (310 mg, yield 88%).

Synthesis of NRX-7018-3

To a stirred solution of NRX-7018-2 (200 mg, 0.308 mmol) in methanol (8 mL) at room temperature was added 10% palladium on carbon (20 mg). The stirring was continued under hydrogen pressure for 18 hrs. After completion of the reaction, the reaction mass was filtered over a celite pad, washed with methanol (20 mL), and the filtrates concentrated under reduced pressure. The crude compound was purified over column chromatography using silica gel (100-200 mesh) and 3% methanol in DCM as eluent to afford NRX-7018-3 (60 mg, yield 30%) as an off-white solid.

Synthesis of NRX-7018

To a stirred solution of NRX-7018-3 (55 mg, 0.084 mmol) in DCM (2.4 mL) at 0° C. was added 5% methanolic HCl (0.6 mL) and the solution was slowly warmed to room temperature and stirred for 2 hours. After completion of the reaction, excess volatiles were removed under reduced pressure. The crude compound was triturated with diethyl ether and dried in vacuo to afford NRX-7018 (50 mg, yield 89.4%) as a white solid.

$^1$H-NMR: (400 MHz, CD$_3$OD): δ 5.48 (s, 1H), 5.31-5.26 (m, 2H), 4.68 (s, 1H), 4.57-4.46 (m, 3H), 4.17 (s, 1H), 3.82-3.30 (m, 5H), 2.33 (d, 6H), 2.06 (d, 5H), 1.92 (s, 1H), 1.62 (m, 5H), 1.39-1.22 (m, 11H).

Mass m/z: 552.3 [M$^+$+1].

Example 12—[$^3$H] MK-801 Binding Assay

This example demonstrates a [$^3$H] MK-801 binding assay that may be used to assess agonistic and/or antagonistic properties of candidate NMDA receptor modulators.

Crude synaptic membranes were prepared from rat forebrains as described in Moskal et al. (2001), "The use of antibody engineering to create novel drugs that target N-methyl-D-aspartate receptors," Curr. Drug Targets, 2:331-45. Male 2-3 month old rats were decapitated without anesthesia by guillotine, and the brains were rapidly removed (~90 sec) and whole cortex and hippocampus dissected on an ice cold platform, frozen on dry ice, and stored at −80° C. Samples were homogenized in 20 volumes of ice cold 5 mM Tris-HCl pH 7.4 by Brinkman Polytron and pelleted 48,000×g for 20 min at 4° C., and washed an additional 3 times as described above. Membranes were then resuspended in 5 mM EDTA and 15 mM Tris-HCl pH 7.4 and incubated for 1 hr at 37° C., membranes pelleted at 48,000×g for 20 min at 4° C., snap frozen in liquid nitrogen, and stored at −80° C. On the day of the experiment, membranes were thawed at room temperature and washed an additional 7 times in ice cold 5 mM Tris-HCl (pH 7.4) as described above. After the last wash, membranes were resuspended in assay buffer (5 mM Tris-acetate pH 7.4), and protein content was determined by the BCA assay.

[$^3$H] MK-801 binding assays were preformed as described in Urwyler et al. (2009), "Drug design, in vitro pharmacology, and structure-activity relationships of 3-acylamino-2-aminopropionic acid derivatives, a novel class of partial agonists at the glycine site on the N-methyl-D-aspartate (NMDA) receptor complex," J. Med. Chem., 52:5093-10. Membrane protein (200 µg) was incubated with varying concentrations of the test compounds ($10^{-3}$-$10^{-17}$M) with 50 µM glutamate for 15 min at 23° C. Assay tubes were then incubated under non-equilibrium conditions with [$^3$H]MK-801 (5 nM; 22.5 Ci/mmol) for 15 min at 23° C. followed by filtration through Whatman GF/B filters using a Brandel M-24R Cell Harvester. Then the tubes were washed three times with assay buffer (5 mM Tris-acetate PH 7.4), and the filters were analyzed by liquid scintillation to calculate the disintegrations per minute (DPM). Zero levels were determined in the absence of any glycine ligand and in the presence of 30 µM 5,7-Dichlorokynurenic acid (5,7-DCKA). Maximal stimulation was measured in the presence of 1 mM glycine. 50 µM glutamate was present in all samples.

For each data point (i.e., a single concentration of the test compound), the % maximal [$^3$H] MK-801 binding was calculated by the following formula:

$$\% \text{ maximal } [^3H] \text{ MK-801 binding} = ((DPM_{(test\ compound)} - DPM_{5,7-DCKA})/(DPM_{1\ mM\ glycine} - DPM_{5,7-DCKA})) \times 100\%$$

The efficacy for each compound, expressed as the % increase in [$^3$H] MK-801 binding, is calculated by fitting the data to a "log(agonist) vs. response (three parameters)" equation using Graph Pad Prism, with the efficacy for the test compound being the best-fit top value.

Example 13—NMDA Receptor (NMDAR) Currents

This example demonstrates an assay for determining the effect of test compounds on NMDAR currents.

Experiments were conducted on hippocampal slices from 14-18 day old Sprague-Dawley rats as described in Zhang et al. (2008) "A NMDA receptor glycine site partial agonist, GLYX-13, simultaneously enhances LTP and reduces LTD at Schaffer collateral-CA1 synapses in hippocampus," Neuropharmacology, 55:1238-50. Whole cell recordings were obtained from CA1 pyramidal neurons voltage clamped at −60 mV, in slices perfused with (artificial cerebrospinal fluid) ACSF containing 0 mM [Mg2+] and 3 mM [Ca2+], plus 10 µM bicuculline and 20 µM CNQX to pharmacologically isolate NMDAR-dependent excitatory postsynaptic currents (EPSCs). Varying concentrations of test compound (10 nM to 1 µM) were bath applied and Schaffer collateral fibers were stimulated with single electrical pulses (80 µs duration) once every 30 s. NMDAR EPSCs were characterized by long rise and decay times, and were fully blocked at the end of each experiment by bath application of the NMDAR-specific antagonist D-2-amino-5-phosphonopentanoic acid (D-AP5; 50 µM). The efficacy of a test compound was calculated as the % increased in NMDAR current from the baseline. The baseline was measured as the NMDAR current before the test compound was applied.

Example 14—Long-Term Potentiation (LTP) Assay

This example demonstrates an assay for determining the effect of test compounds on LTP.

Hippocampal slices from 14-18 day old Sprague-Dawley rats were transferred to an interface recording chamber and continuously perfused at 3 ml/min with oxygenated ACSF at 32±0.5° C. Low resistance recording electrodes were made from thin-walled borosilicate glass (1-2 MΩ after filling with ACSF) and inserted into the apical dendritic region of the Schaffer collateral termination field in *stratum radiatum* of the CA1 region to record field excitatory postsynaptic potentials (fEPSPs). A bipolar stainless steel stimulating electrode (FHC Co.) was placed on Schaffer collateral-commissural fibers in CA3 *stratum radiatum*, and constant current stimulus intensity adjusted to evoke approximately half-maximal fEPSPs once each 30 s (50-100 pA; 100 ms duration). fEPSP slope was measured by linear interpolation from 20%-80% of maximum negative deflection, and slopes confirmed to be stable to within ±10% for at least 10 min before commencing an experiment. Long-term potentiation (LTP) was induced by a high frequency stimulus train (3×100 Hz/500 ms; arrow) at Schaffer collateral-CA1 synapses in control (vehicle), untreated slices, or slices pre-treated with test compound (10 nM to 100 µM). Signals were recorded using a Multiclamp 700B amplifier and digitized with a Digidata 1322 (Axon Instruments, Foster City, Calif.). Data were analyzed using pClamp software (version 9, Axon Instruments) on an IBM-compatible personal computer. The efficacy was calculated as the % increase in long-term potentiation measured for slices pre-treated with test compound as compared to vehicle.

Example 15—Porsolt Test

This example demonstrates the Porsolt test for assessing test compounds for antidepressant activity.

Experiments were conducted as described in Burgdorf et al. (2009) "The effect of selective breeding for differential rates of 50-kHz ultrasonic vocalizations on emotional behavior in rats," Devel. Psychobiol., 51:34-46. Male Sprague-Dawley rats (2-3 month old) were dosed with test compound (0.3 to 30 mg/kg; intravenously via tail vein injection, or per os via gastric gavage) or vehicle (1 ml/kg sterile saline, or 1 ml/kg DMSO for 2,5-diazaspiro[3.4] octan-1-one) in a blind manner 1 hr before testing. Animals were placed in a 46 cm tall×20 cm in diameter clear glass tube filled to 30 cm with tap water at room temperature (23° C.±0.5° C.) for 5 min on the test day. All animals were towel dried after each swimming session by the experimenter. Water was changed after every other animal. Animals were videotaped and total duration (sec) of floating behavior (as defined as the minimal movement required in order to maintain the animal's head above the water) was quantified by a blind experimenter.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A peptidyl compound of the formula:

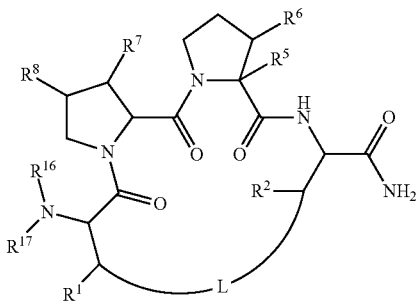

wherein:
$R^1$ and $R^2$ are independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —C(O)$R^x$; —$CO_2(R^x)$; —C(O)N$(R^x)_2$; —C(N$R^x$)N$(R^x)_2$; —OC(O)$R^x$; —$OCO_2R^x$; —OC(O)N$(R^x)_2$; —N$(R^x)_2$; —SO$R^x$; —S(O)$_2R^x$; —N$R^x$C(O)$R^x$; —N$R^x$C(O)N$(R^x)_2$; —N$R^x$C(O)O$R^x$; —N$R^x$C(N$R^x$)N$(R^x)_2$; and —C$(R^x)_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ are independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ are independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^{16}$ and $R^{17}$ are independently selected from the group consisting of hydrogen; $C_1$-$C_6$ alkyl, optionally substituted by one or more substituents each independently selected from the group consisting of halogen, oxo, and hydroxyl; $C_{2-6}$alkenyl, optionally substituted by one or more substituents each independently selected from the group consisting of halogen, oxo, and hydroxyl; $C_{2-6}$alkynyl, optionally substituted by one or more substituents each independently selected from the group consisting of halogen, oxo, and hydroxyl; $C_{3-6}$cycloalkyl, optionally substituted by one or more substituents each independently selected from the group consisting of $C_{1-6}$alkyl, halogen, oxo, and hydroxyl; phenyl, optionally substituted by one or more substituents each independently selected from the group consisting of $C_{1-6}$alkyl, $C_{1-6}$alkoxy; halogen, and hydroxyl; —C(O)$R^x$; —$CO_2(R^x)$; —C(O)N$(R^x)_2$; —C(N$R^x$)N$(R^x)_2$; and —C$(R^x)_3$; wherein each occurrence of $R^x$ is independently selected from the group consisting of hydrogen; halogen; $C_1$-6alkyl; $C_{2-6}$alkenyl; $C_{2-6}$alkynyl; $C_{3-6}$cycloalkyl; and phenyl; or $R^{16}$ and $R^{17}$, together with N, form a 4-6 membered heterocyclic ring, optionally substituted by one or more substituents each independently selected from the group consisting of $C_{1-6}$alkyl, halogen, oxo, and hydroxyl;

L is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted aryl; and substituted or unsubstituted heteroaryl; and pharmaceutically acceptable salts, stereoisomers, metabolites, and hydrates thereof.

2. The compound of claim 1, wherein L is —O—($C_1$-$C_{20}$ alkyl)-O—.

3. The compound of claim 1, wherein L is —O—[($C_1$-$C_6$ alkyl)-O]$_n$—, wherein n is 1, 2, 3, 4, 5 or 6.

4. The compound of any of claim 1, wherein at least one of $R^1$ and $R^2$ is hydroxyl.

5. The compound of any of claim 1, wherein at least one of $R^1$ and $R^2$ is $C_1$-$C_6$ alkyl.

6. The compound of any of claim 1, wherein at least one of $R^5$ and $R^6$ is —$C_1$-$C_6$ alkyl-Ar.

7. The compound of any of claim 1, wherein at least one of $R^5$ and $R^6$ is —(CH$_2$)—Ar.

8. The compound of any of claim 1, wherein at least one of $R^5$ and $R^6$ is -Q-phenyl.

9. The compound of any of claim 1, wherein at least one of $R^5$ and $R^6$ is hydrogen.

10. The compound of claim 1 represented by:
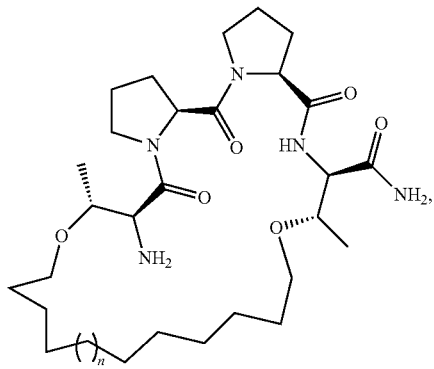
wherein n is an integer from 0-9.
11. The compound of claim 1 represented by:
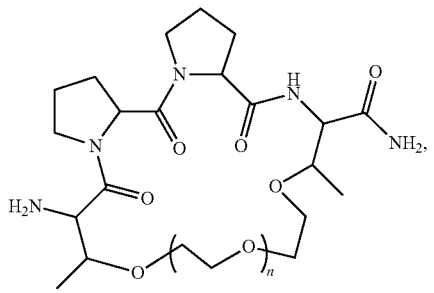
wherein n is an integer from 1-5.
12. The compound of claim 1 represented by:
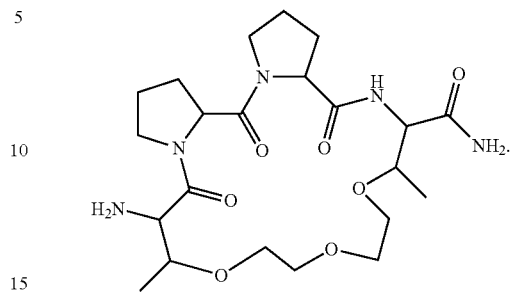
13. The compound of claim 1 represented by:
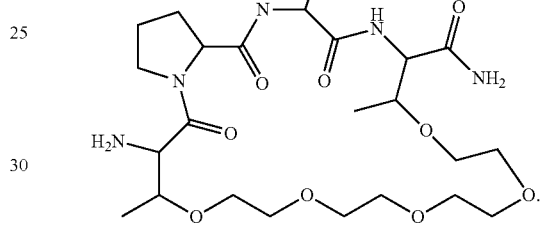
* * * * *